(12) United States Patent
Pavlov et al.

(10) Patent No.: US 9,918,743 B2
(45) Date of Patent: Mar. 20, 2018

(54) FACET INTERFERENCE CAGE

(75) Inventors: Paul Pavlov, Nijmegen (NL); Tom Overes, Oberdorf (CH); Robert Frigg, Oberdorf (CH); Philippe Lindenmann, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 635 days.

(21) Appl. No.: 13/465,508

(22) Filed: May 7, 2012

(65) Prior Publication Data

US 2013/0123923 A1    May 16, 2013

Related U.S. Application Data

(60) Provisional application No. 61/484,441, filed on May 10, 2011, provisional application No. 61/527,878, (Continued)

(51) Int. Cl.
*A61F 2/44* (2006.01)
*A61B 17/70* (2006.01)
(Continued)

(52) U.S. Cl.
CPC .......... *A61B 17/70* (2013.01); *A61B 17/1671* (2013.01); *A61B 17/7064* (2013.01); *A61F 2/442* (2013.01); *A61F 2/4405* (2013.01); *A61F 2/4455* (2013.01); *A61F 2/4611* (2013.01); *A61B 17/0206* (2013.01); *A61B 17/1697* (2013.01); *A61B 2090/034* (2016.02); *A61F 2/30767* (2013.01); *A61F 2002/30029* (2013.01); *A61F 2002/3093* (2013.01); *A61F 2002/30306* (2013.01); *A61F 2002/30471* (2013.01);
(Continued)

(58) Field of Classification Search
CPC . A61B 17/7062; A61B 17/7064; A61B 17/70; A61B 17/0206; A61B 17/1671; A61B 17/1697; A61F 2/4405
USPC ................... 606/246–249, 90, 86 A, 99, 914
See application file for complete search history.

(56) References Cited

U.S. PATENT DOCUMENTS 5,716,415 A * 2/1998 Steffee .................... A61F 2/447
                                                                  623/17.16
6,547,795 B2    4/2003 Schneiderman
(Continued)

FOREIGN PATENT DOCUMENTS

CN         101296670       10/2008
DE         101 35 771       2/2003
(Continued)

OTHER PUBLICATIONS

"Surgical Technique Manual", DePuy Spine, Inc., Jan. 2012, 25 sheets.

*Primary Examiner* — Tatiana Nobrega
*Assistant Examiner* — Jessica Weiss
(74) *Attorney, Agent, or Firm* — Baker & Hostetler LLP

(57) ABSTRACT

An implant includes a body sized and shaped for insertion into a facet joint, the implant including a first bone fixation element receiving opening extending through a portion thereof along a first axis oriented so that, when the implant is received within a facet joint in a desired configuration, a bone fixation element inserted into the first bone fixation element receiving opening will extend into a first one of the vertebra forming the facet joint.

55 Claims, 37 Drawing Sheets

Related U.S. Application Data filed on Aug. 26, 2011, provisional application No. 61/602,927, filed on Feb. 24, 2012.

(51) Int. Cl.

| | | |
|---|---|---|
| *A61B 17/16* | (2006.01) | |
| *A61F 2/46* | (2006.01) | |
| *A61B 17/02* | (2006.01) | |
| *A61F 2/30* | (2006.01) | |
| *A61B 90/00* | (2016.01) | |

(52) U.S. Cl.
CPC .............. *A61F 2002/30542* (2013.01); *A61F 2002/30576* (2013.01); *A61F 2002/30578* (2013.01); *A61F 2002/30785* (2013.01); *A61F 2002/30787* (2013.01); *A61F 2002/30828* (2013.01); *A61F 2002/30879* (2013.01); *A61F 2002/30904* (2013.01); *A61F 2002/4687* (2013.01)

(56) References Cited

U.S. PATENT DOCUMENTS

| | | | | |
|---|---|---|---|---|
| 6,635,086 | B2* | 10/2003 | Lin | ............... A61F 2/4455 623/17.11 |
| 6,972,019 | B2* | 12/2005 | Michelson | ............... 606/86 A |
| 7,101,398 | B2 | 9/2006 | Dooris et al. | |
| 7,326,248 | B2* | 2/2008 | Michelson | ............... 623/17.11 |
| 7,369,360 | B2 | 7/2008 | Lieberman | |
| 7,655,044 | B2 | 2/2010 | Kwak | |
| 7,695,514 | B2 | 4/2010 | Kwak | |
| 7,744,630 | B2 | 6/2010 | Lancial | |
| 7,799,054 | B2 | 9/2010 | Kwak et al. | |
| 7,828,824 | B2 | 11/2010 | Kwak et al. | |
| 8,043,334 | B2 | 10/2011 | Fisher et al. | |
| 8,070,783 | B2 | 12/2011 | Kwak et al. | |
| 8,133,261 | B2 | 3/2012 | Fisher et al. | |
| 8,142,503 | B2 | 3/2012 | Malone | |
| 8,197,513 | B2 | 6/2012 | Fisher et al. | |
| 8,287,597 | B1* | 10/2012 | Pimenta | ............... A61F 2/4611 623/17.16 |
| 9,486,327 | B2* | 11/2016 | Martynova | ............... A61F 2/442 |
| 2004/0102774 | A1* | 5/2004 | Trieu | ............... A61B 17/7097 606/86 A |
| 2005/0055096 | A1 | 3/2005 | Serhan et al. | |
| 2005/0159746 | A1 | 7/2005 | Grob et al. | |
| 2005/0240188 | A1 | 10/2005 | Chow et al. | |
| 2006/0004448 | A1 | 1/2006 | Casey | |
| 2006/0036323 | A1 | 2/2006 | Carl | |
| 2006/0064099 | A1 | 3/2006 | Pavlov et al. | |
| 2006/0089717 | A1 | 4/2006 | Krishna et al. | |
| 2006/0287729 | A1 | 12/2006 | Segal et al. | |
| 2007/0016195 | A1 | 1/2007 | Winslow et al. | |
| 2007/0016196 | A1 | 1/2007 | Winslow et al. | |
| 2007/0135814 | A1 | 6/2007 | Farris | |
| 2008/0161810 | A1 | 1/2008 | Melkent | |
| 2008/0140085 | A1* | 6/2008 | Gately | ............... A61F 2/4465 606/99 |
| 2008/0249569 | A1 | 10/2008 | Waugh et al. | |
| 2008/0255622 | A1 | 10/2008 | Mickiewicz et al. | |
| 2008/0262623 | A1* | 10/2008 | Bagga | ............... A61F 2/442 623/17.16 |
| 2009/0024166 | A1 | 1/2009 | Carl et al. | |
| 2009/0062921 | A1* | 3/2009 | Michelson | ............... A61F 2/44 623/17.16 |
| 2009/0192613 | A1* | 7/2009 | Wing | ............... A61F 2/4465 623/17.11 |
| 2009/0306671 | A1 | 12/2009 | McCormack et al. | |
| 2010/0076493 | A1 | 3/2010 | Fauth et al. | |
| 2010/0145397 | A1 | 6/2010 | Overes et al. | |
| 2011/0004247 | A1 | 1/2011 | Lechmann et al. | |
| 2011/0098710 | A1 | 4/2011 | Spratt et al. | |
| 2011/0172769 | A1* | 7/2011 | Ganem | ............... A61F 2/30771 623/17.11 |
| 2012/0010662 | A1 | 1/2012 | O'Neil et al. | |
| 2013/0123793 | A1* | 5/2013 | Kehres et al. | ............... 606/104 |

FOREIGN PATENT DOCUMENTS

| | | | |
|---|---|---|---|
| JP | 2002-508679 | 3/2002 | |
| JP | 2004-209248 | 7/2004 | |
| JP | 2007-518524 | 7/2007 | |
| JP | 2008-522787 | 7/2008 | |
| JP | 2009-519113 | 5/2009 | |
| JP | 2010-115477 | 5/2010 | |
| JP | 2010-523216 | 7/2010 | |
| WO | WO 00/23015 | 4/2000 | |
| WO | 00/53126 | 9/2000 | |
| WO | WO 2006/065774 | 6/2006 | |
| WO | 2006101837 | 9/2006 | |
| WO | 2007/098288 | 8/2007 | |
| WO | WO 2007/098288 | * 8/2007 | ............... A61F 2/44 623/17.16 |

* cited by examiner

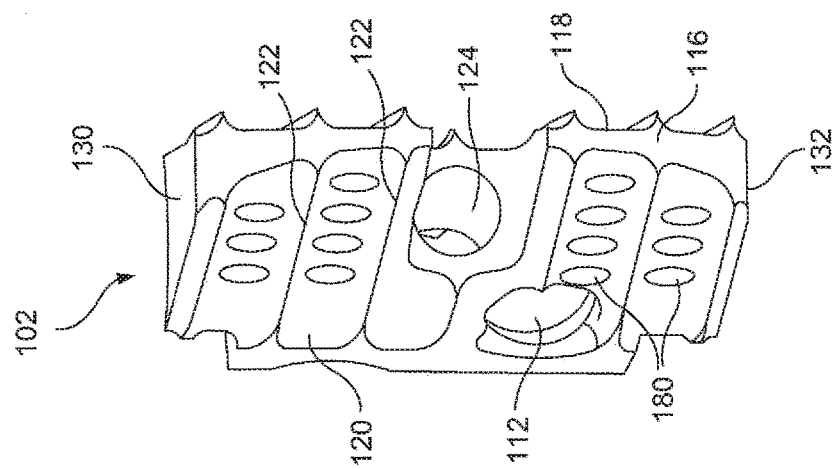
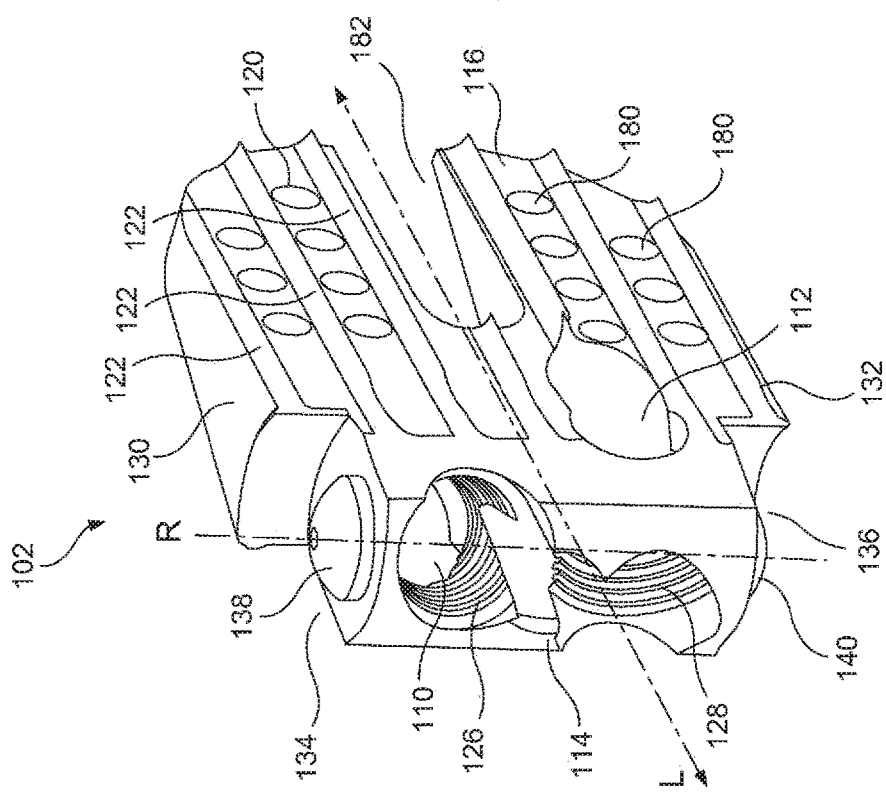

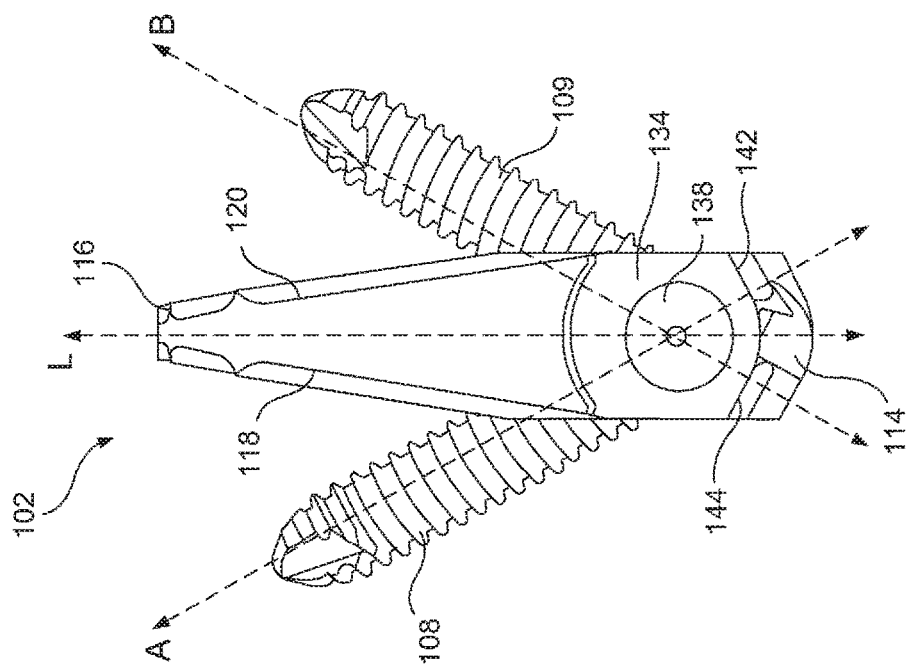
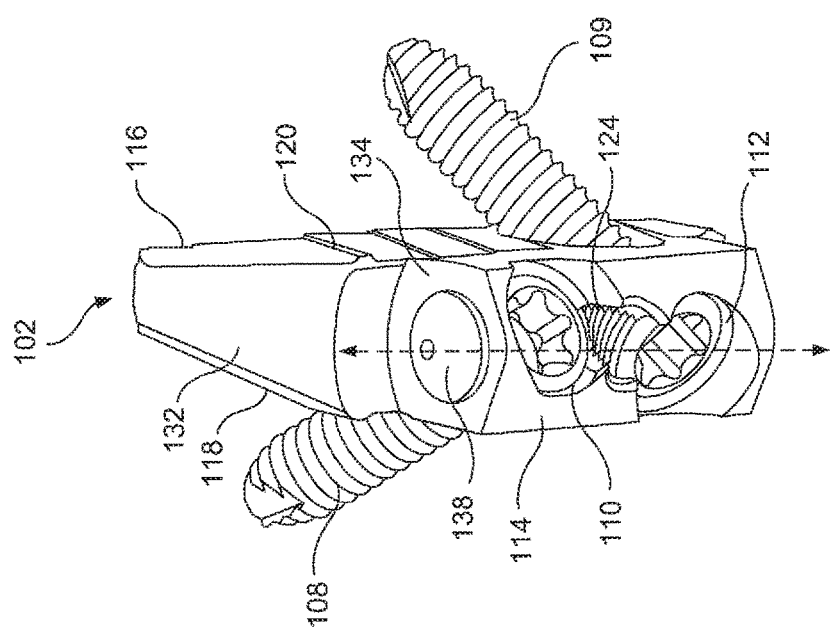
FIG. 6
FIG. 5

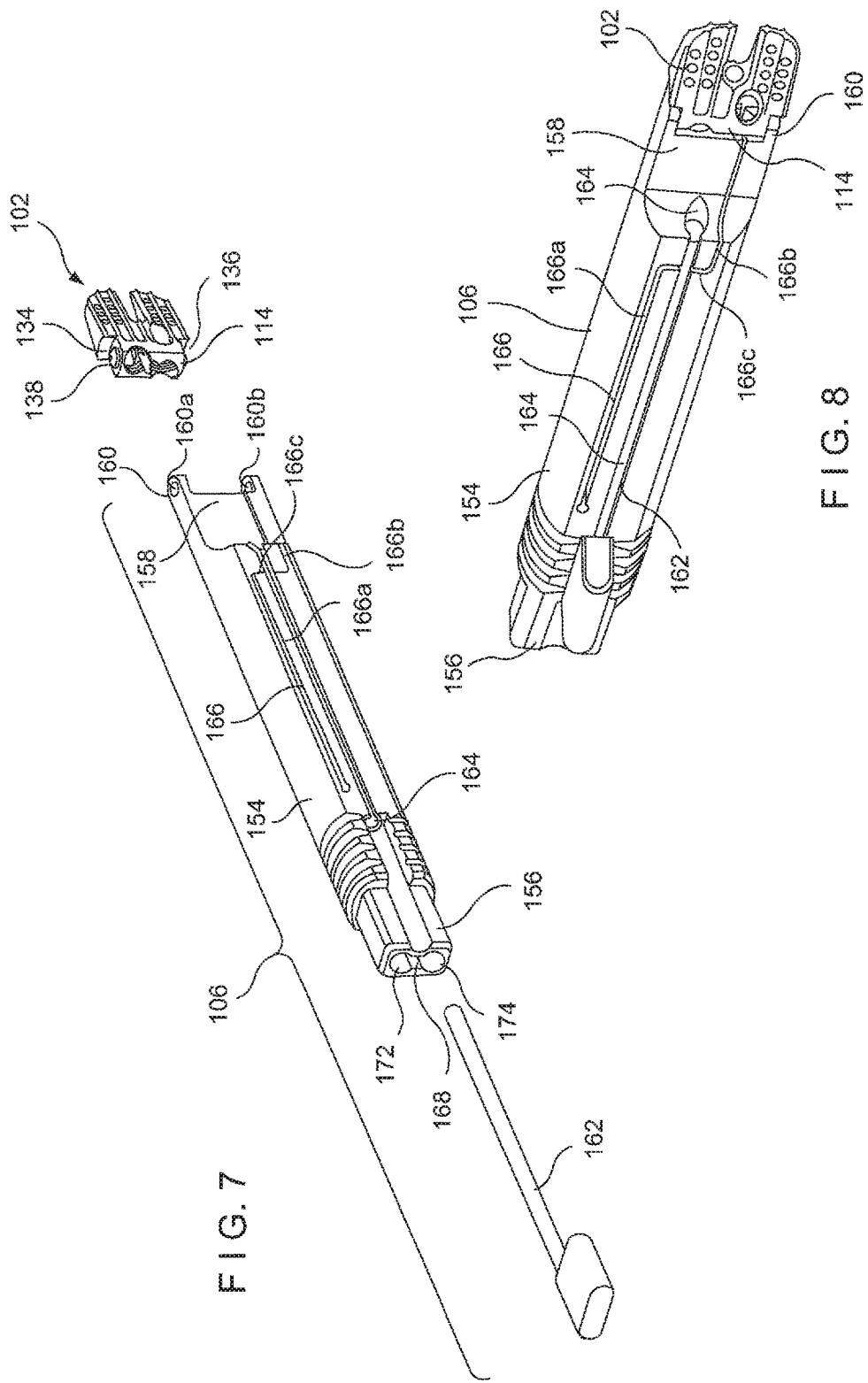

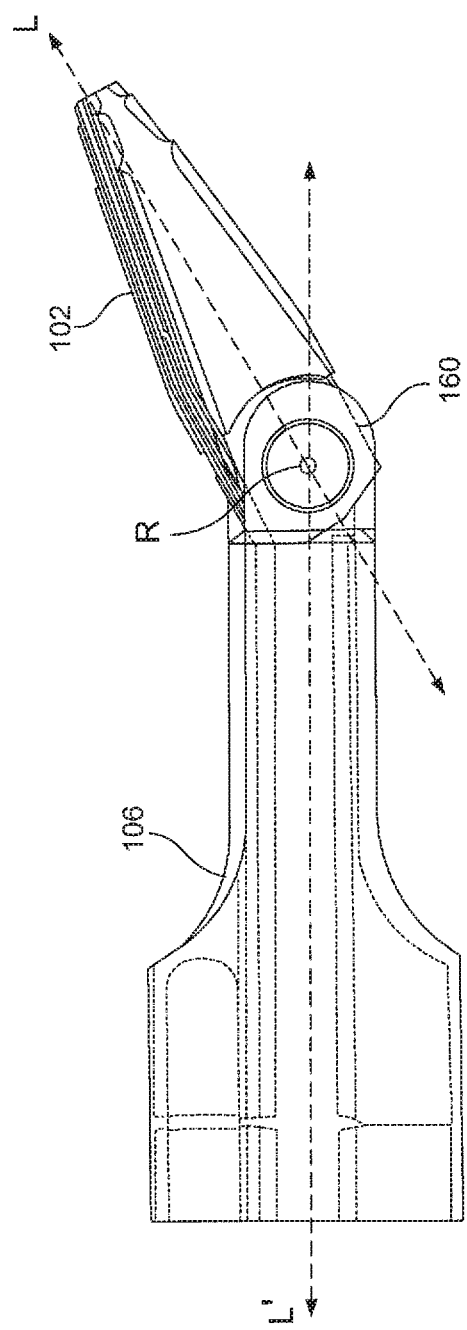

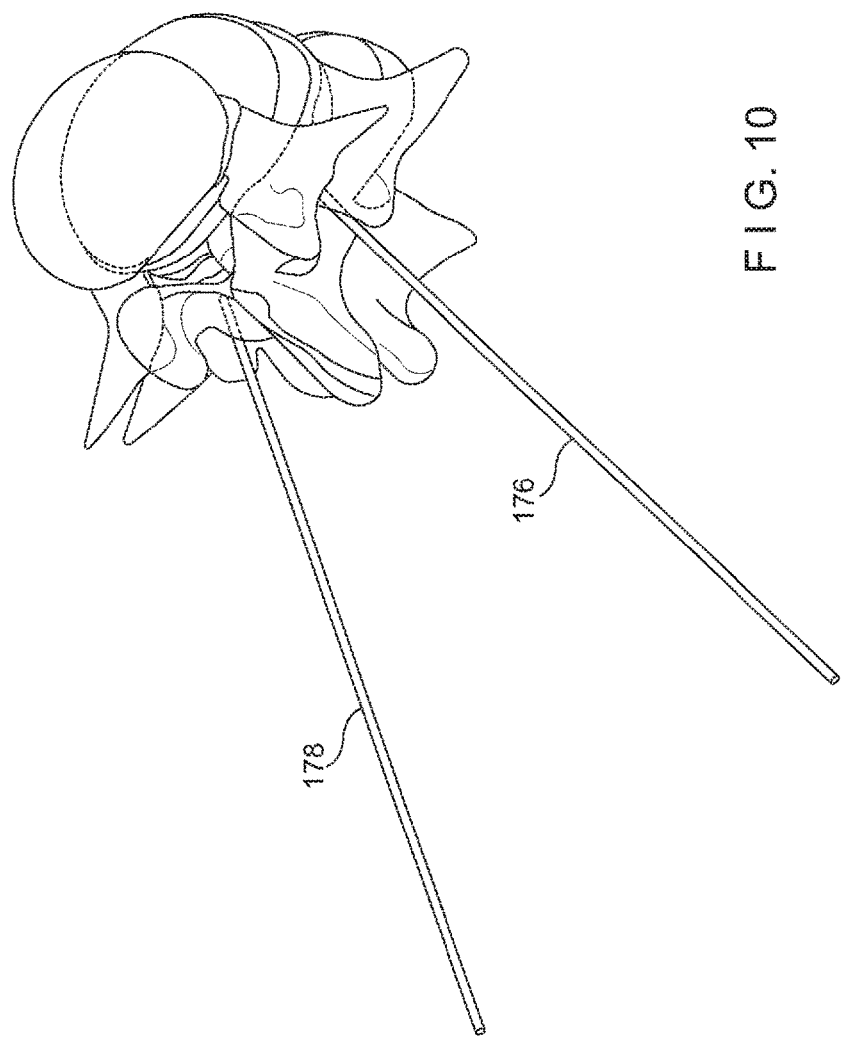

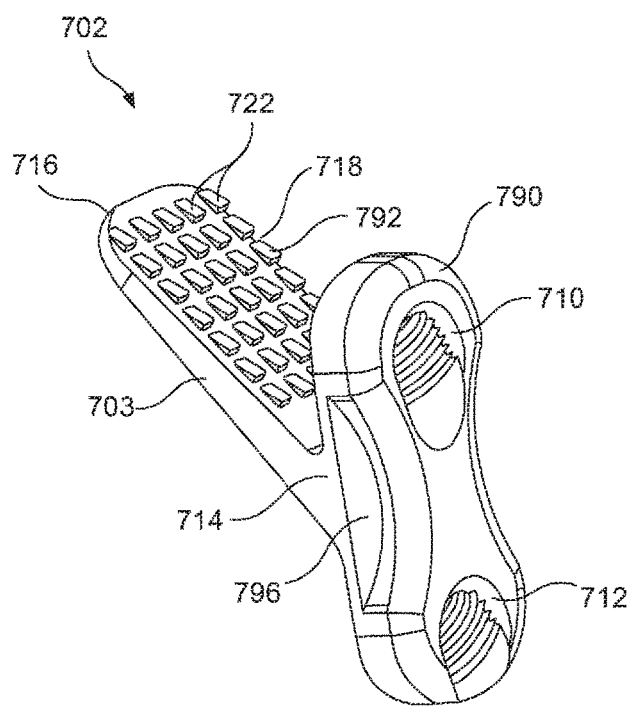
FIG. 45
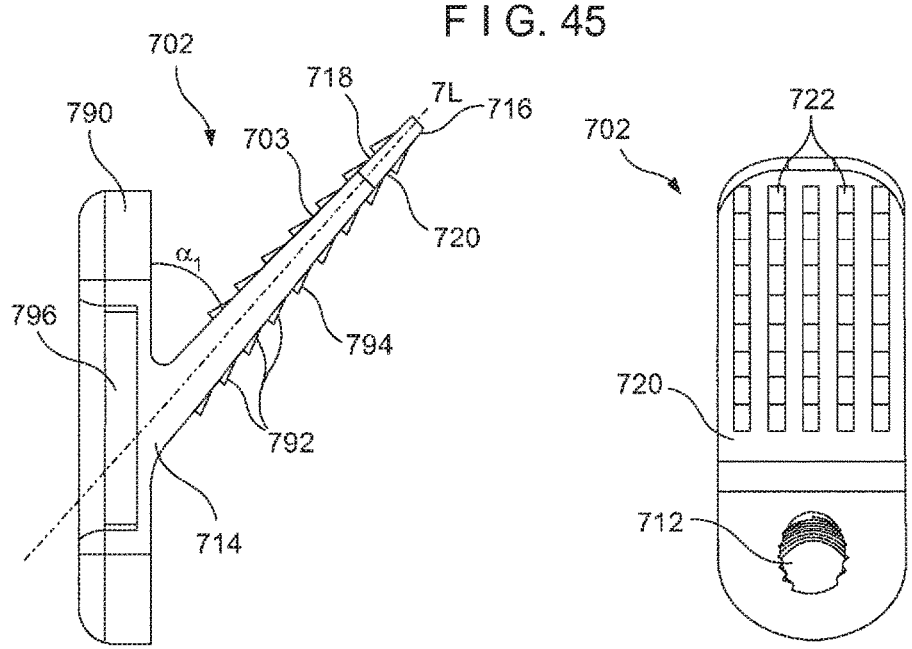
FIG. 46
FIG. 47

US 9,918,743 B2

FACET INTERFERENCE CAGE

PRIORITY CLAIM

The present application claims priority to U.S. Provisional Application Ser. No. 61/484,441 entitled "Implant and Tool" filed on May 10, 2011, U.S. Provisional Application Ser. No. 61/527,878 entitled "Facet Interference Cage" filed on Aug. 26, 2011 and U.S. Provisional Application Ser. No. 61/602,927 entitled "Facet Interference Cage" filed on Feb. 24, 2012, the entire disclosure of which are incorporated herein by reference.

BACKGROUND

Posterior spinal fusion may be achieved using, for example, screws, rods and/or plates to fix two or more adjacent vertebrae relative to one another and facilitate fusion. Pedicle screws are used to add extra support to prevent the vertebrae from moving while fusing. These implants and/or fixation devices may be bulky, causing patient-discomfort and requiring time-consuming, invasive procedures.

SUMMARY OF THE INVENTION

The present invention is directed to an implant comprising a body sized and shaped for insertion into a facet joint, the implant including a first bone fixation element receiving opening extending through a portion thereof along a first axis oriented so that, when the implant is received within a facet joint in a desired configuration, a bone fixation element inserted into the first bone fixation element receiving opening will extend into a first one of the vertebra forming the facet joint.

BRIEF DESCRIPTION OF THE DRAWINGS

FIG. 3 shows a perspective view of the implant of FIG. 2;

FIG. 4 shows another perspective view of the implant of FIG. 2;

FIG. 5 shows a perspective view of the implant of FIG. 2 with bone fixation elements inserted through openings thereof;

FIG. 6 shows a top plan view of the implant of FIG. 2 with bone fixation elements inserted through openings thereof;

FIG. 7 shows a perspective view of an aiming guide and implant of the system of FIG. 1;

FIG. 8 shows another perspective view of the aiming guide and implant of FIG. 7;

FIG. 9 shows an enlarged view of a distal portion of the aiming guide and implant of FIG. 7;

FIG. 10 shows a perspective view of guide wires inserted into a facet joint according to an exemplary method of the present invention;

FIG. 45 shows a first perspective view of an implant according to yet another exemplary embodiment of the invention;

FIG. 46 shows a second perspective view of the implant of FIG. 45;

FIG. 47 shows a third perspective view of the implant of FIG. 45;

DETAILED DESCRIPTION

Figure 1:
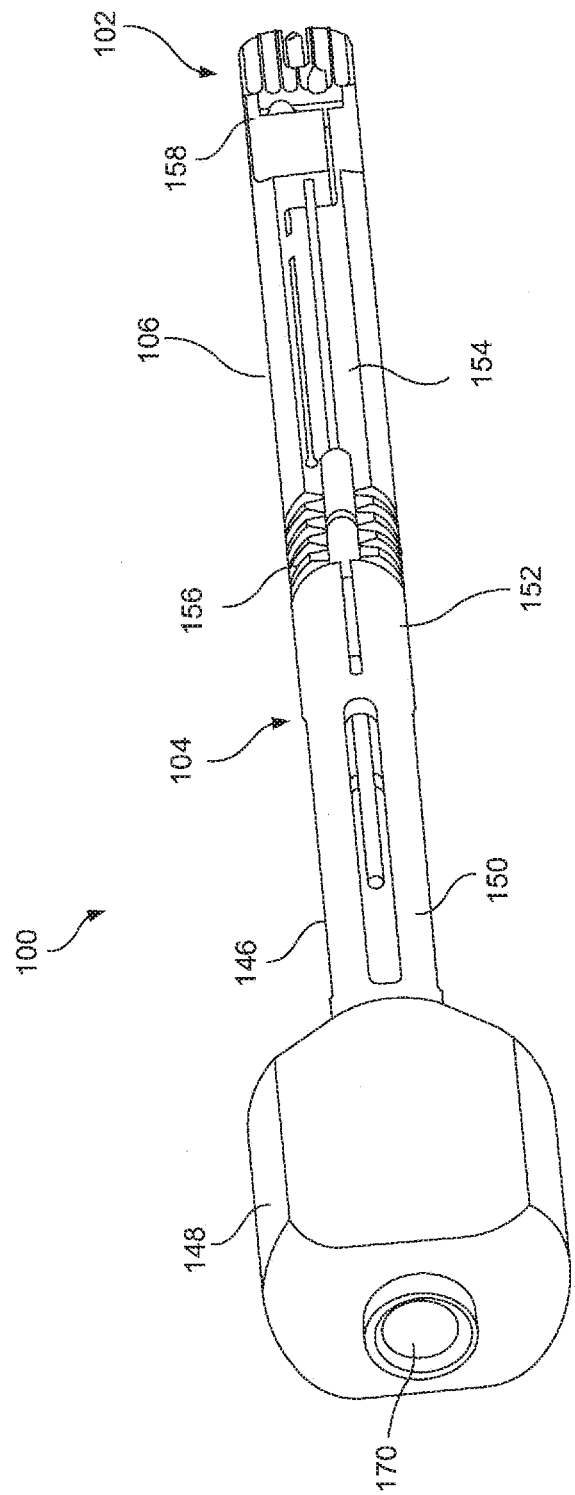
FIG. 1 shows a perspective view of a system according to an exemplary embodiment of the present invention.

The present invention may be further understood with reference to the following description and the appended drawings, wherein like elements are referred to with the same reference numerals. The present invention relates to bone treatment devices and, in particular, relates to a minimally invasive posterior fusion device. Exemplary embodiments of the present invention describe a system and method for posterior spinal fusion, including an implant shaped for insertion into a facet joint of adjacent vertebra along with an insertion tool to facilitate proper insertion and fixation thereof. It will be understood by those of skill in the art that the system and method of the present invention utilize a faster, less invasive technique which requires less muscle stripping and does not require the usage of pedicle screws for stabilization. It should be noted that the terms "proximal" and "distal" as used herein, are intended to refer to a direction toward (proximal) and away from (distal) a surgeon or other user of the device.

Figure 2:
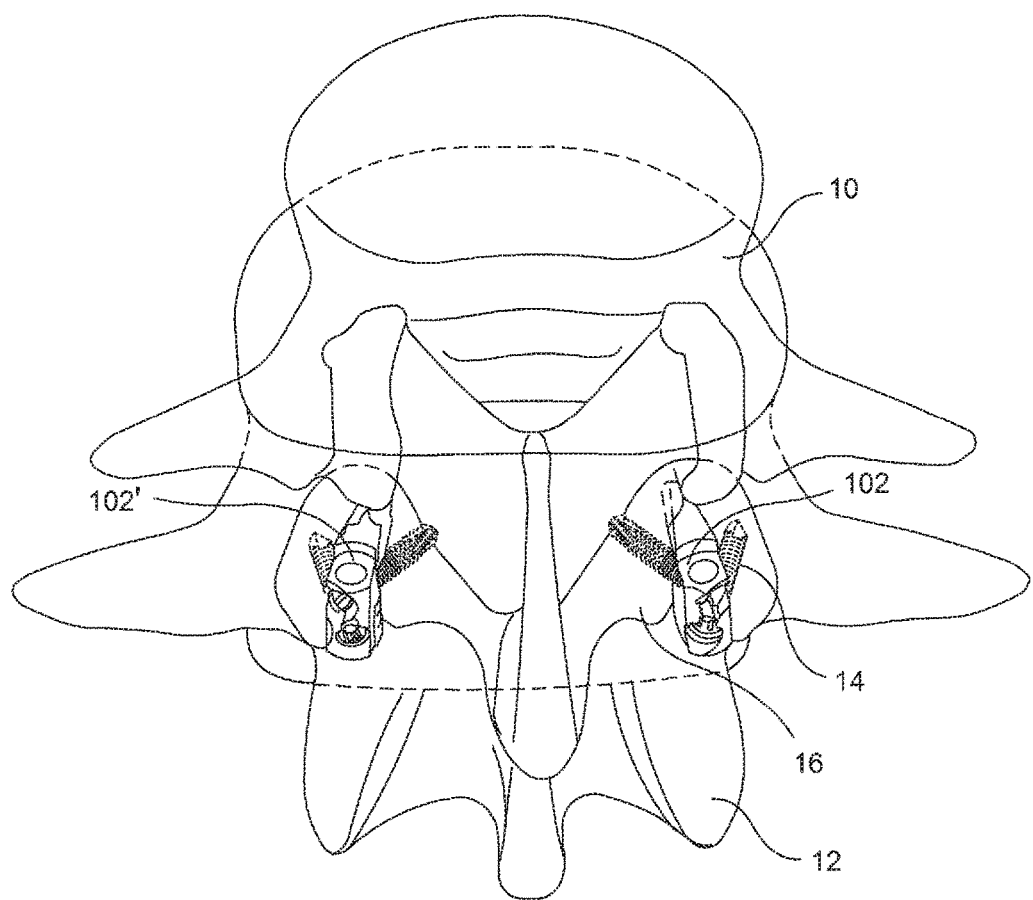
FIG. 2 shows a perspective view of an implant of the system of FIG. 1, implanted in a facet joint.

As shown in FIGS. 1-9, a system 100 for posterior fusion comprises an implant 102 sized and shaped for insertion into a facet joint to facilitate fusion of first and second vertebrae 10, 12. As shown in FIGS. 1-2, the system 100 further comprises an insertion tool 104 including an impactor 146 for facilitating impaction of the implant 102 into the facet joint (i.e., the joint between a superior articular process 14 of the second vertebra 12 and an inferior articular process 16 of the first vertebra 10 directly above it) and an aiming guide 106 for guiding first and second bone fixation elements 108, 109 through first and second holes 110, 112, respectively, of the implant 102 to fix the implant 102 to the vertebrae 10, 12. It will be understood by those of skill in the art that each spinal motion segment (e.g., vertebra 10, 12) includes two facet joints (i.e., a right side and a left side) such that the system 100 may include a second implant 102'. The implant 102, as described below, may be configured to be implanted into one of the two facet joints (e.g., the right facet joint) while the second implant 102' may be configured to be implanted into the other of the two facet joints (e.g., the left facet joint). Thus, although the second implant 102' is not described in detail, it will be understood by those of skill in the art that the second implant 102' may be substantially similar to the implant 102 and, in particular, may be a mirror image of the implant 102. Where the system 100 includes two implants 102, 102', the first and second implants 102, 102' may be color-coded and/or labeled to indicate whether the implants 102, 102' are configured for the right or left facet joint.

As shown in FIGS. 3-6, the implant 102 is substantially wedge-shaped extending along a longitudinal axis L and tapering from a first end 114 which, when implanted into the facet joint in a desired configuration, faces a posterior side of the spine, to a second end 116 which, when implanted into the facet joint faces a ventral side of the spine. The tapered second end 116 facilitates insertion of the implant 102 into the facet joint. The implant 102 is defined by first and second substantially planar surfaces 118, 120 which extend from the first end 114 to the second end 116 at an angle with respect to the longitudinal axis L to form the tapered wedge-shape, and third and fourth lateral surfaces 130, 132 which connect the first and second surfaces 118, 120. When implanted into the facet joint, the first surface 118 engages the inferior articular process 16 of the first vertebra 10 while the second surface 120 engages the superior articular process 14 of the second vertebra 12. The first and second surfaces 118, 120 each include a plurality of ribs 122 projecting therefrom and extending from the first end 114 to the second end 116 to guide the implant 102 into the joint and facilitate engagement with the first and second vertebra 10, 12. However, those skilled in the art will understand that the extent of some or all of the ribs 122 may be changed as desired.

Furthermore, the first and second surfaces 118, 120 may be roughened and/or treated with a coating to facilitate bone ingrowth. The implant 102 also includes a plurality of openings 180 extending therethrough from the first surface 118 to the second surface 120 to promote bony growth therethrough, increasing stability after fusion. In a further embodiment, the implant 102 may also include a cut out 182 extending proximally from the second end 116 (i.e., toward the first end 114) and extending therethrough from the first surface 118 to the second surface 120. The cut out 182 minimizes sharp edges that may be present to accommodate a central opening 124 through which a K-wire or similar device may be positioned.

The implant 102 also includes a central opening 124 extending therethrough from the first end 114 to the second end 116 along the longitudinal axis L. The central opening 124 is sized and shaped to accommodate a guide wire therethrough such that the implant 102 may be slid along a guide wire inserted into the facet joint. The first and second holes 110, 112 of this embodiment extend through the implant 102 on opposing sides of the central opening 124. The first hole 110 extends therethrough from the first end 114 to the first surface 118 such that a first hole axis of the first hole 110 is angled with respect to the longitudinal axis L. As would be understood by those skilled in the art, the first hole 110 may include a threading 126 along all or a portion of an inner surface thereof for engaging a threading on a head of a first bone fixation element 108 inserted therethrough. The first bone fixation element 108 may be received in the first hole 110 along the first hole axis A such that a shaft thereof is inserted into the inferior articular process of the first vertebra 10. The second hole 112 extends therethrough from the first end 114 to the second surface 120 along a second hole axis B of the second hole 112 angled with respect to the longitudinal axis L in a direction opposite the first hole axis A. For example, the first axis A may be angled with respect to the longitudinal axis L at an angle between approximately 10° and 45° and, more particularly, between 25° and 30° while the second axis B may be angled with respect to the longitudinal axis L at an angle between approximately −10° and −45° and, more particularly, between −25° and −30°. Similar to the first hole 110, the second hole 112 may include threading 128 along all or a portion of an inner surface thereof for engaging a threading on a head of a second bone fixation element 109 inserted therethrough. The second bone fixation element 109 may be received within the second hole 112 along the second hole axis B such that a shaft thereof is inserted into the inferior articular process of the second vertebra 12. In one exemplary embodiment, a portion of the first and second holes 110, 112 at the first end 114 may be open to and overlap with the central opening 124, as shown. In this embodiment, a guide wire inserted through the central opening 124 prevents bone fixation elements 108, 109 from being inserted through the first and second openings 110, 112. In another embodiment, one or both of the first and second holes 110, 112 may be formed as a distinct hole, separated from the central opening 124.

The first end 114 is configured for attachment to the aiming guide 106. For example, third and fourth surfaces 130, 132 of this embodiment include recesses 134, 136, respectively, at the first end 114 which permit a portion of the aiming guide 106 to be received therein. The recesses 134, 136 may also include protrusions 138, 140, respectively, which extend therefrom to engage a portion of the aiming guide 106 received therein. The protrusions 138, 140 may, for example, be dome shaped to facilitate engagement with the aiming guide 106 while also permitting the aiming guide 106 to pivot with respect to the implant 102 about an axis of rotation R. Thus, the protrusions 138, 140 may be coaxial with the axis of rotation R. The axis R may be substantially perpendicular to the third and fourth lateral surfaces 130, 132. Although the protrusions 138, 140 are described as dome-shaped, it will be understood by those of skill in the art that the protrusions 138, 140 may be any of a variety of shapes so long as the protrusions 138, 140 permit engagement with the aiming guide 106 and pivoting of the implant 102 relative thereto. The first end 114 according to this embodiment of the invention also includes first and second abutting surfaces 142, 144, respectively, extending substantially parallel to the rotation axis R and at an angle with respect to the longitudinal axis L to define a maximum angle of pivot of the implant 102 relative to the aiming guide 106. The angles of the first and second abutting surfaces 142, 144 correspond to the angle of the first and second axes A, B of the first and second openings 110, 112, respectively.

As shown in FIG. 1, the impactor 146 and the aiming guide 106 of the insertion tool 104 are releasably coupled to one another via, for example, a friction fit. The impactor 146 includes a head 148 and a shaft 150 extending distally therefrom to a distal end 152 configured to be attached to the aiming guide 106. The distal end 152 may, for example, receive a portion of the aiming guide 106 therein. The impactor 146 also includes a channel 170 extending therethrough along a longitudinal axis for receiving a guide wire therethrough. The head 148 may have a larger cross-sectional area than the shaft 150, providing a surface on which a force may be exerted to impact the implant 102 into the facet joint.

As shown in FIGS. 7-8, the aiming guide 106 includes a body 154 extending along a longitudinal axis L' from a proximal end 156 configured to be attached to the distal end 152 of the impactor 146 to a distal end 158 configured to be coupled to the implant 102. The body 154 further includes a central channel 168 extending longitudinally therethrough from the proximal end 156 to the distal end 158 such that when the aiming guide 106 and/or impactor 146 is coupled to the implant 102, the central opening 124 of the implant 102 is aligned with the central channel 168 of the aiming guide 106 and the channel 170 of the impactor 146 to receive a guide wire therethrough. The body 154 also includes a first guide channel 172 and a second guide channel 174, each of which extend longitudinally therethrough from the proximal end 156 to the distal end 158 in a position corresponding to the first and second openings 110, 112, respectively, of the implant 102 such that when coupled thereto, drills and/or bone fixation elements 108, 109 may be guided therethrough into the first and second openings 110, 112. The first and second guide channels 172, 174 may overlap with the central channel 168 depending on a configuration of the first and second openings 110, 112 of the implant 102.

The proximal end 156 may, for example, have a reduced cross-section area sized and shaped to be received within the distal end 152 of the impactor 146 via a friction fit. The aiming guide 106 and the impactor 146 are coupled such that the longitudinal axes thereof are substantially coaxial with one another. The distal end 158 of the aiming guide 106 may include jaws 160 including first and second jaw members 160a, 160b extending distally therefrom on opposing sides of the longitudinal axis L'. The jaws 160 receive a portion of the first end 114 between the first and second jaw members 160a, 160b seated within the recesses 134, 136 of the implant 102. The jaw members 160a, 160b also include recesses along inner surfaces thereof sized and shaped to receive the protrusions 138, 140 therein to engage the implant 102. The body 154 may be at least partially formed of a compliant material and include a slot 166 extending along a portion thereof from an exterior surface to an interior surface of the body 154 to permit the jaw members 160a, 160b to be flexed apart from one another such that the first end 114 of the implant 102 may be received therebetween and the arms 160 extended over the protrusions 138, 140 to be "snapped" thereover. Upon coupling the aiming guide 106 to the implant 102, the arms 106 may revert to an initial, undeformed configuration to hold the first end 114 therebetween. The slot 166 may, for example, be substantially Z-shaped including first and second portion 166a, 166b extending substantially parallel to the longitudinal axis L' and a third portion 166c connecting the first and second portions 166a, 166b to form a continuous slot 166.

The aiming guide 106 according to this embodiment further includes a locking rod 162 which may be inserted into a locking channel 164 extending along an exterior of the body 154 to lock the arms 160 in the undeformed configuration, preventing the implant 102 from being inadvertently disengaged therefrom. The locking channel 164 extends along the body 154 and intersects with the slot 166 such that the when the locking rod 162 is inserted therethrough, the jaws 160 are prevented from moving apart from one another, thus locking the aiming guide 106 and the implant 102 together. The locking channel 164 may, for example, extend longitudinally along the body 154 to intersect with the third portion 166c of the slot 166. It will be understood by those of skill in the art that the system 100 may be utilized in a minimally invasive procedure via a small incision along a portion of the spine corresponding to a position of the vertebrae 10, 12. Thus, if the implant 102 were inadvertently disengaged from the aiming guide 106, the implant 102 would be difficult to locate via the small incision. To unlock the aiming guide 106 and the implant 102, the locking rod 162 may be removed from the locking channel 162 such that the jaws 160 may be flexed apart from one another by the slot 166.

As shown in FIG. 9, once the aiming guide 106 and the implant 102 have been coupled to one another, the aiming guide 106 is pivotable with respect to the implant 102 about the rotation axis R such that the longitudinal axis L of the implant 102 may be angled with respect to the longitudinal axis L' of the aiming guide 106. The aiming guide 106 may be pivoted between a neutral position in which the central channel 168 is aligned with the central opening 124 of the implant 102 (i.e., the longitudinal axes L, L' are coaxial), a first position in which the first guide channel 172 is substantially coaxial and aligned with the first opening 110 and a second position in which the second guide channel 174 is substantially coaxial and aligned with the second opening 112. The first and second positions are defined by the first and second abutting surfaces 142, 144 of the implant 102. In particular, in the first position, the first abutting surface 142 abuts a portion of the distal end 158 of the body 154 of the aiming guide 106, preventing the aiming guide 106 from moving beyond a desired maximum angle of pivot relative to the implant 102 in a first direction. In the second position, the second abutting surface 144 abuts a portion of the distal end 158, preventing the aiming guide 106 from moving beyond a desired maximum angle of pivot relative to the implant 102 in a second direction.

Figure 11:
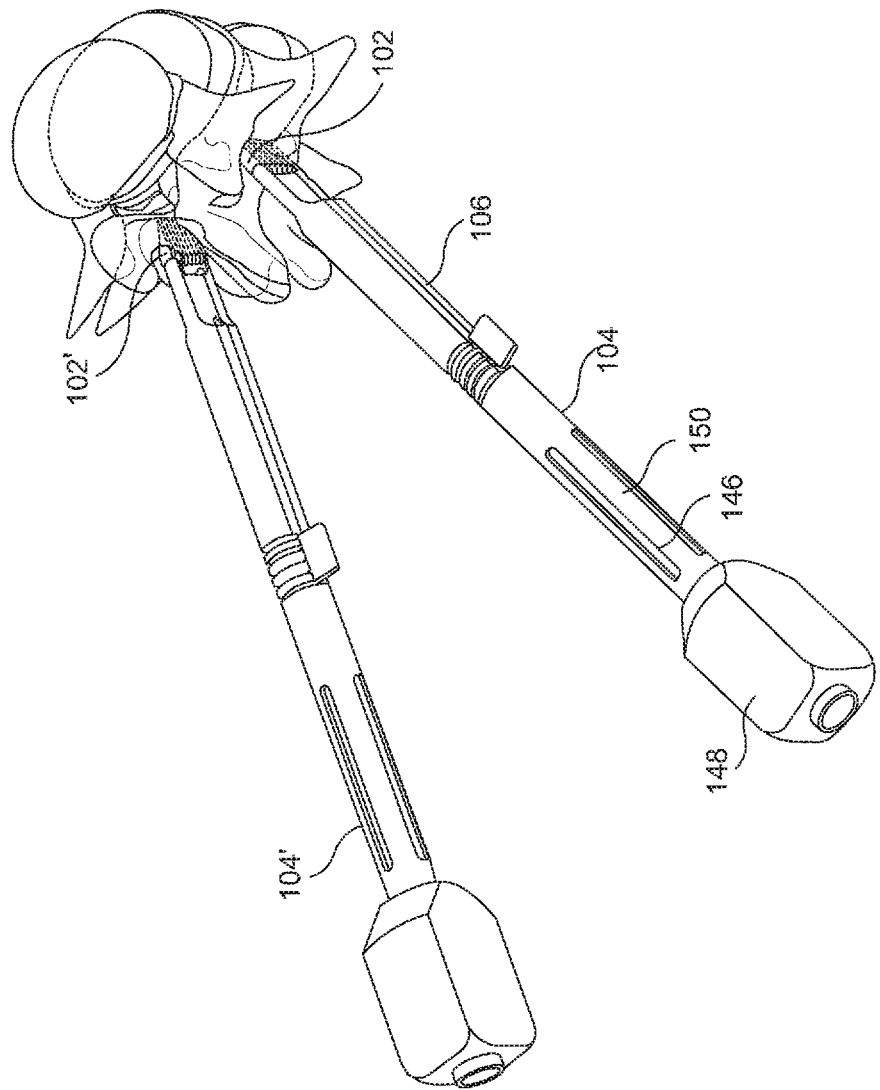
FIG. 11 shows a perspective view of an insertion tool and implant slid over the guide wires according to the method of FIG. 10.

FIGS. 10-16 show an exemplary surgical method using the system 100. As shown in FIG. 10, the method comprises inserting a first guide wire 176 into a facet joint between the first and second vertebrae 10, 12. For example, the first guide wire 176 may be inserted into a right facet joint. If it is desired to insert an implant in each of the right and left facet joints, a second guide wire 178 may be inserted into the other facet joint (e.g., left facet joint). The insertion tool 104 may be coupled to the implant 102, as described above, such that longitudinal axes of the impactor 146, the aiming guide 106 and the implant 102 are substantially coaxial with one another. The locking rod 162 may be inserted into the locking channel 164 to ensure that the aiming guide 106 and the implant 102 remain coupled during the entire surgical process. The coupled insertion tool 104 and the implant 102 may then be slid over the first guide wire 176, as shown in FIG. 11, such that the first guide wire 176 is received within the central openings 124 of the implant 102 and the central channels 170, 168 of the impactor 146 and the aiming guide 106 such that the implant 102 is in the neutral position relative to the aiming guide 106. The guide wire 176 ensures that the impactor 146 and the implant 102 are aligned such that an impacting tool may be used to impact the implant 102 by applying a force to the head 148 of the impactor 146 such that the implant 102 penetrates a capsule covering the facet joint and is inserted into the facet joint. The tapered second end 116 of the implant 102 facilitates penetration of the capsule. A second insertion tool 104', which is substantially similar to the insertion tool 104, may be coupled to the second implant 102' and similarly slid over the second guide wire 178. It will be understood by those of skill in the art that although they will not be discussed in detail, all of the steps described in regard to the insertion tool 104 and the implant 102 may be repeated for the second insertion tool 104' and the second implant 102'. It will also be understood by those of skill in the art that although the figures show the implant 102' and the insertion tool 104', it may be desired to implant only a single implant 102 in either the right or left facet joint.

Figure 12:
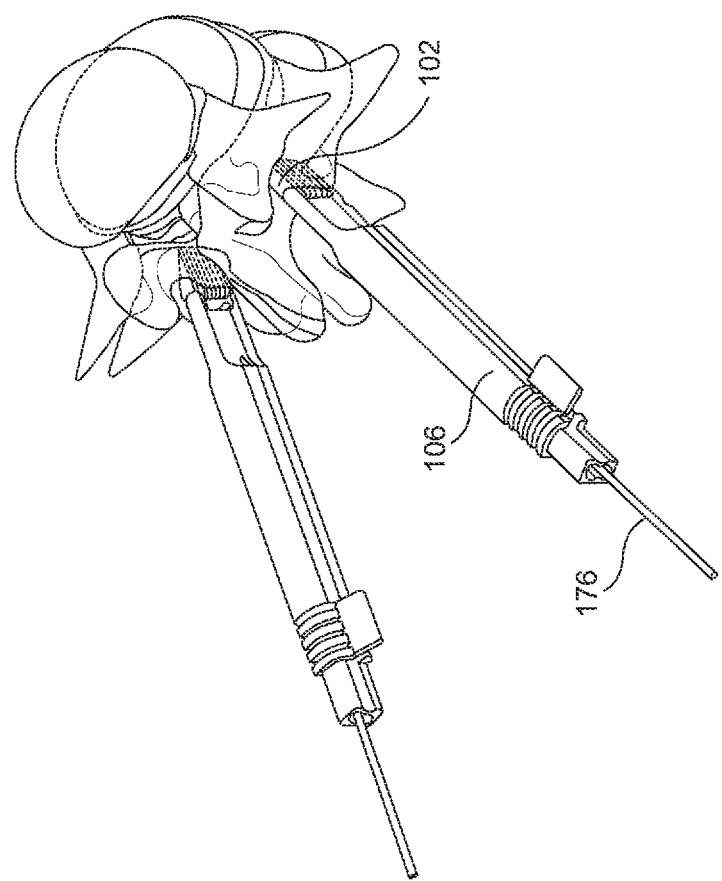
FIG. 12 shows a perspective view of the aiming guide attached to the implant according to the method of FIG. 10.
Figure 13:
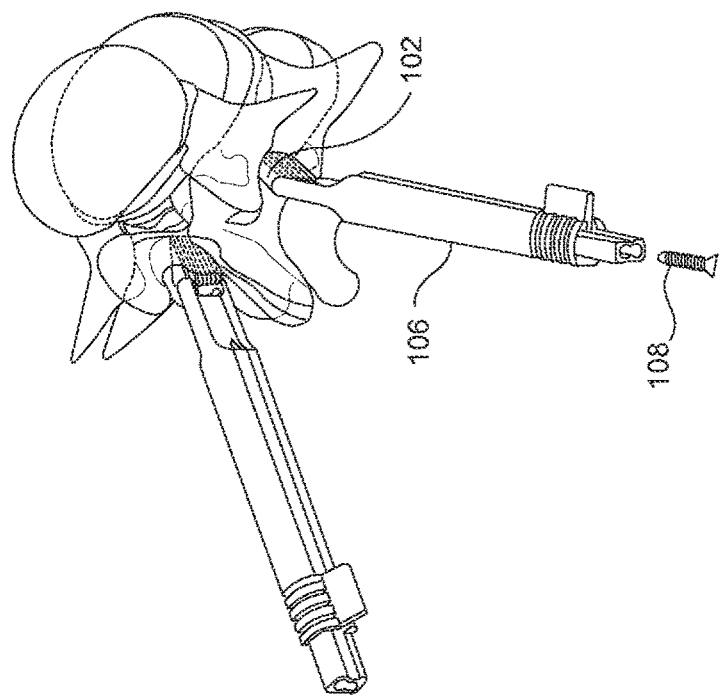
FIG. 13 shows a perspective view of the aiming guide in a first position relative to the implant according to the method of FIG. 10.

Once the implant 102 has been impacted into the facet joint, the impactor 146 may be disengaged from the aiming guide 106 such that only the aiming guide 106 and the implant 102 remain mounted over the first guide wire 176, as shown in FIG. 12. The first guide wire 176 may then be removed such that the aiming guide 106 may be pivoted with respect to the implant 102. The aiming guide 106 is pivoted about the rotation axis R of the implant 102 until the aiming guide 106 is in the first position (i.e., the first abutting surface 142 of the implant 102 abuts a portion of the distal end 158 of the aiming guide 106), as shown in FIG. 13, and the first guide channel 172 is aligned with the first opening 110. A drill or awl may be inserted through the first guide channel 172 to drill a hole into inferior process 16 of the first vertebra 10 in alignment with the first axis A of the first opening 110. The bone fixation element 108 may be inserted through the first guide channel 172 and into the first opening 110 such that a head of the fixation element 108 engages the first opening 110 while a shaft extends into the inferior process 16 fixing the implant 102 to the first vertebra 10.

Figure 14:
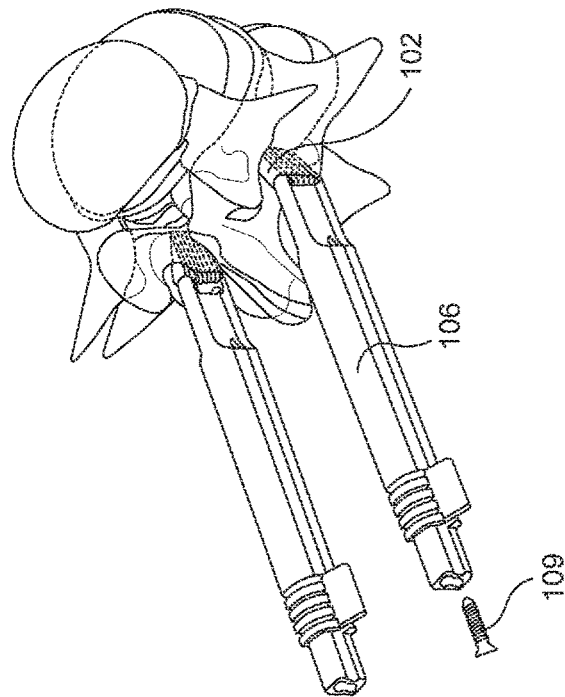
FIG. 14 shows a perspective view of the aiming guide in a second position relative to the implant according to the method of FIG. 10.
Figure 16:
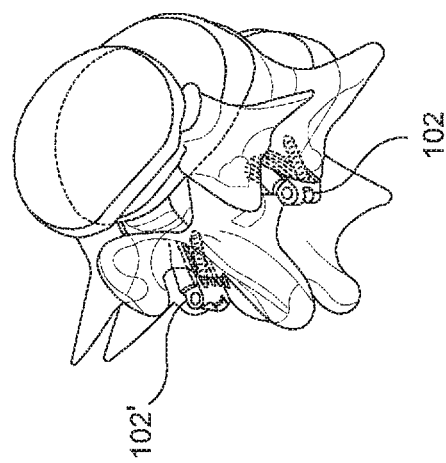
FIG. 16 shows a perspective view of an addition implant fixed within another facet joint according to the method of FIG. 10.
Figure 15:
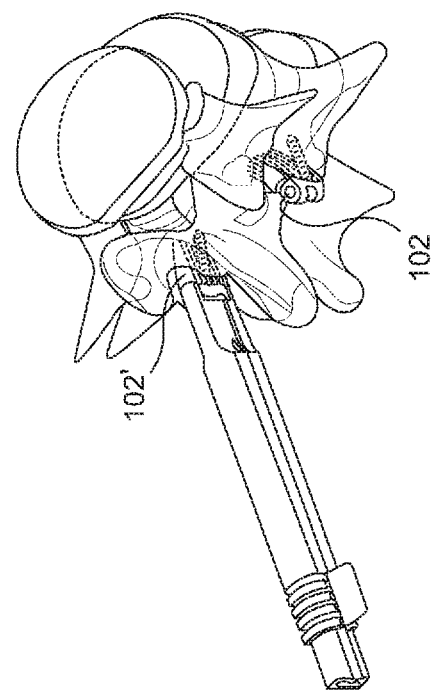
FIG. 15 shows a perspective view of the implant fixed within the facet joint according to the method of FIG. 10.

As shown in FIG. 14, the aiming guide 106 may then be pivoted to the second position relative to the implant 102 (i.e., the second abutting surface 144 of the implant 102 abuts a portion of the distal end 158 of the aiming guide 106) such that the second guide channel 174 is aligned with the second opening 112 of the implant 102. A hole may be drilled in the superior articular process 14 of the second vertebra 12 via the second guide channel 174 and the bone fixation element 109 inserted therethrough to engage the second opening 112. A head of the bone fixation element 109 engages the second opening while a shaft of the bone fixation element 109 extends into the superior articular process 14 such that the implant 102 is fixed to the second vertebra 12. It will be understood by those of skill in the art, however, that in an alternate embodiment, the second bone fixation element 109 may be inserted into the second opening 112 prior to insertion of the first bone fixation element 108 into the first opening 110. Once both the first and second bone fixation elements 108, 109 have been inserted into the first and second openings 110, 112, respectively, the aiming guide 106 is moved to the neutral position and the locking rod 162 removed therefrom so that the aiming guide 106 may be decoupled from the implanted implant 102, as shown in FIG. 15. The above-described steps may be similarly repeated for the implant 102' using an aiming guide 106' of the insertion tool 104', until the implant 102' is fixed within the second facet joint, as shown in FIG. 16. It will be understood by those of skill in the art that the implantation of both implants 102, 102' is not required. It may be desired to implant a single implant 102 in either of the right or left facet joint.

Figure 18:
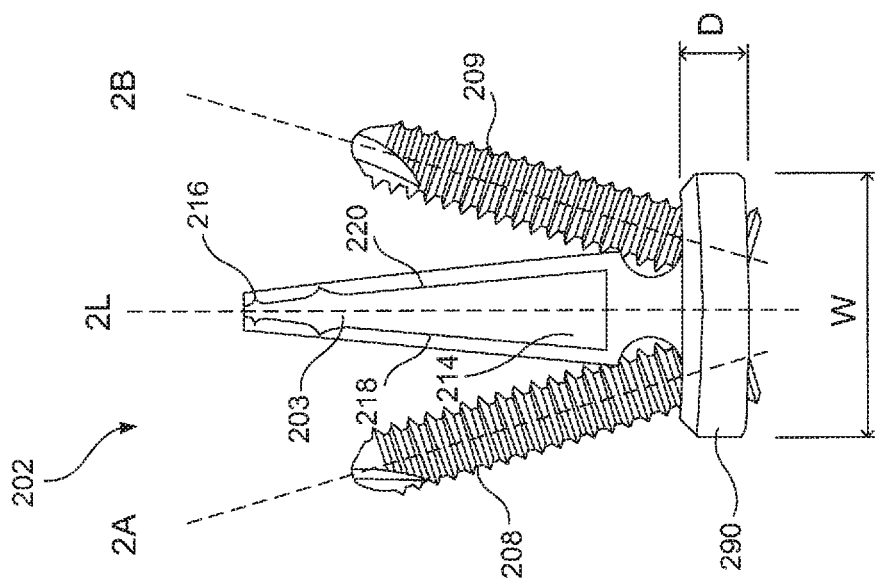
FIG. 18 shows a top plan view of the implant of FIG. 17.
Figure 17:
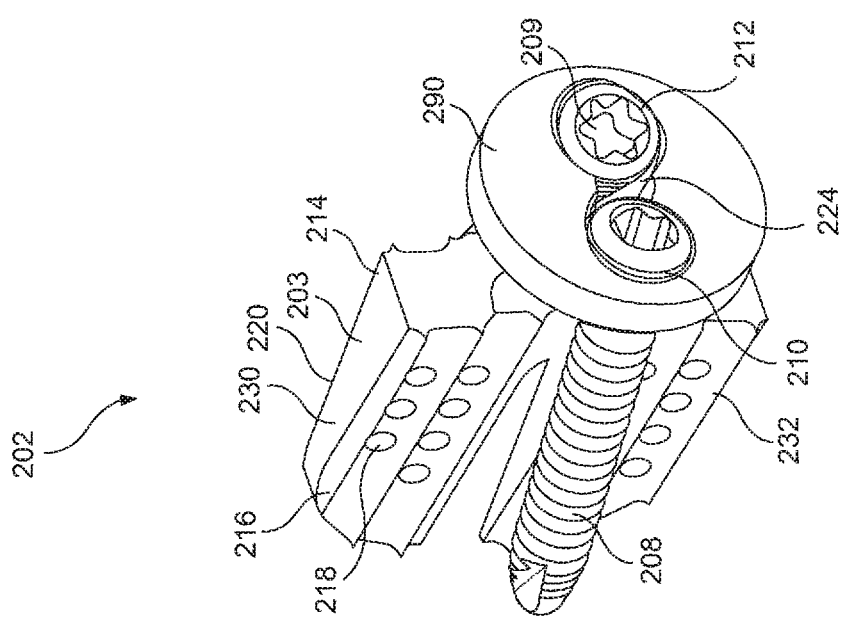
FIG. 17 shows a perspective view of an implant according to another exemplary embodiment of the present invention.

As shown in FIGS. 17-18, an implant 202 according to another exemplary embodiment may be substantially similar to the implant 102, described above in regard to the system 100. Similarly to the implant 102, the implant 202 may have a body 203 that is substantially wedge-shaped, tapering from a first end 214 to a second end 216 along a longitudinal axis 2L. The implant 202 is defined by first and second substantially planar surfaces 218, 220 which extend from the first end 214 to the second end 216 at an angle with respect to the longitudinal axis 2L to form the tapered wedge shape, and third and fourth lateral surfaces 230, 232 which connect the first and second surfaces 218, 220. The implant 202, however, further includes a head portion 290 attached to the first end 214 of the body 203 and having a width (i.e., a distance of the head portion 290 extending across the longitudinal axis 2L) greater than a width W of the first end 214 of the body 203 (i.e., a distance between the first and second surfaces 218, 220 at the first end 214). For example, the width may be approximately 10 mm. In one embodiment, the head portion 290 may be substantially circular such that width corresponds to a diameter of the head portion 290. It will be understood by those of skill in the art, however, that the head portion 290 may be any of a variety of shapes and sizes so long as the head portion 290 is wider than the first end 214 of the body 203. The larger width of the head portion 290 acts as a stop to prevent the head portion 290 from being inserted into the facet joint. Thus, the implant 202 may be easily removed, if so desired. The head portion 290 may also include a coupling feature configured for attachment to an insertion and/or removal instrument as would be understood by those skilled in the art.

Similarly to the implant 102, the implant 202 includes a central opening 224 extending through the head portion 290 and the body 203 along the longitudinal axis 2L to accommodate a guide wire therethrough along with first and second openings 210, 212 extending therethrough to accommodate bone fixation elements 208, 209. The first and second openings 210, 212, however, extend only through the head portion 290. In particular, the first opening 210 extends through the head portion 290 along a first axis 2A, which is angled with respect to the longitudinal axis 2L in a first direction such that the bone fixation element 208 may be inserted through the first opening 210 along the first axis 2A and into a first vertebra of the facet joint. The second opening 212 extends through the head portion 290 along a first axis 2B, which is angled with respect to the longitudinal axis 2L in a second direction opposite the first direction such that the bone fixation element 209 may be inserted through the second opening 212 along the first axis 2B and into a second vertebra of the facet joint. For example, the central axis, the first axis 2A may be angled with respect to the longitudinal axis 2L at an angle of between approximately 5° and 45° and, more particularly, between 10° and 20° while the second axis 2B may be angled with respect to the longitudinal axis 2L at an angle of between approximately 10° and 20°. In an exemplary embodiment, having an angle of approximately 15°, this angle permits a surgeon or other user to insert the bone fixation elements 208, 209 through the first and second holes 210, 212, respectively, without the use of an aiming guide, as discussed above in regard to the system 100. It will be understood by those of skill in the art, however, that the first and second axes 2A, 2B may be at any of a variety of angles with respect to the longitudinal axis 2L so long as the bone fixation elements 208, 209 received within the openings 210, 212 therealong are inserted into first and second vertebrae of the facet joint.

A depth D of the head portion 290 (i.e., a distance of the head portion 290 along the longitudinal axis 2L) may be between approximately 2.0 to 3.0 mm such that the first and second holes 210, 212 may receive heads of the first and second bone fixation elements 208, 209, respectively, therein. Inner surfaces of the holes 210, 212 may include threading to engage threads along the heads of the first and second bone fixation elements 208, 209 so that shafts thereof extend into the first and second vertebrae of the facet joint to fix the implant 202 thereto.

The implant 202 may also be substantially symmetrical about the longitudinal axis 2L such that the implant 202 may be utilized for either facet joint—i.e., a left side or a right side—and would not require a "left" and "right" side configuration. In particular, the body 203 may have a substantially symmetrical wedge shape, and the first and second axes 2A, 2B of the first and second openings 210, 212 may also be symmetrical about the longitudinal axis 2L. The implant 202 may be implanted into the facet joint by sliding the implant 202 over a guide wire received within the central opening 224 until the head portion 290 prevents further movement thereof. The guide wire may then be removed so that bone fixation elements 208, 209 may be inserted through the first and second openings 210, 212, respectively, and into the first and second vertebrae to fix the implant 202 thereto.

Figure 19:
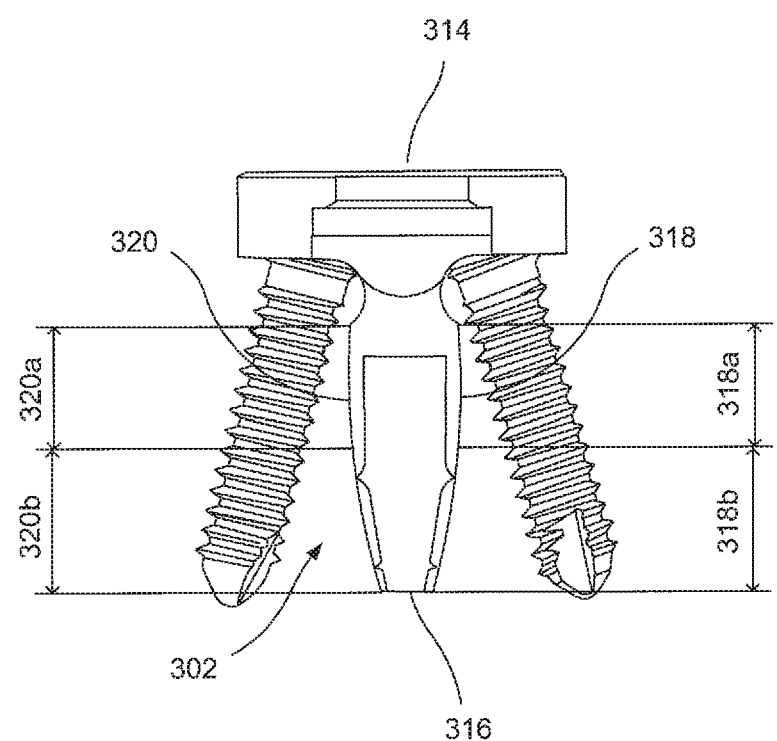
FIG. 19 shows a top plan view of an implant according to yet another embodiment of the invention.
Figure 20:
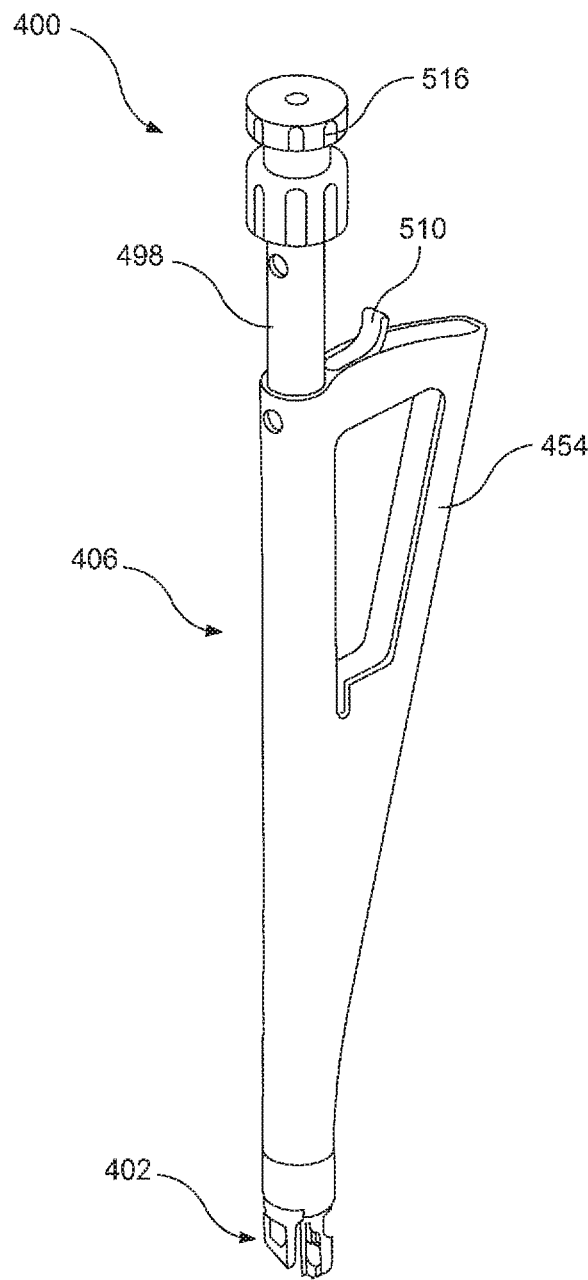
FIG. 20 shows a perspective view of a system according to another exemplary embodiment of the present invention.
Figure 21:
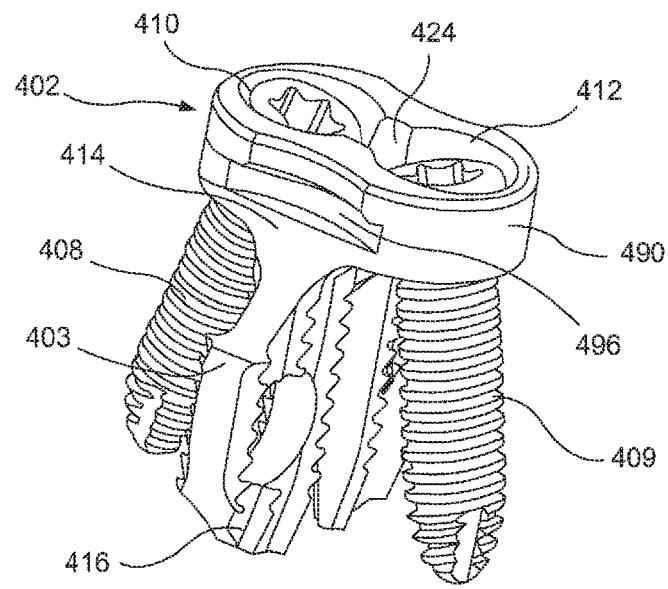
FIG. 21 shows a perspective view of an implant of the system of FIG. 20.
Figure 22:
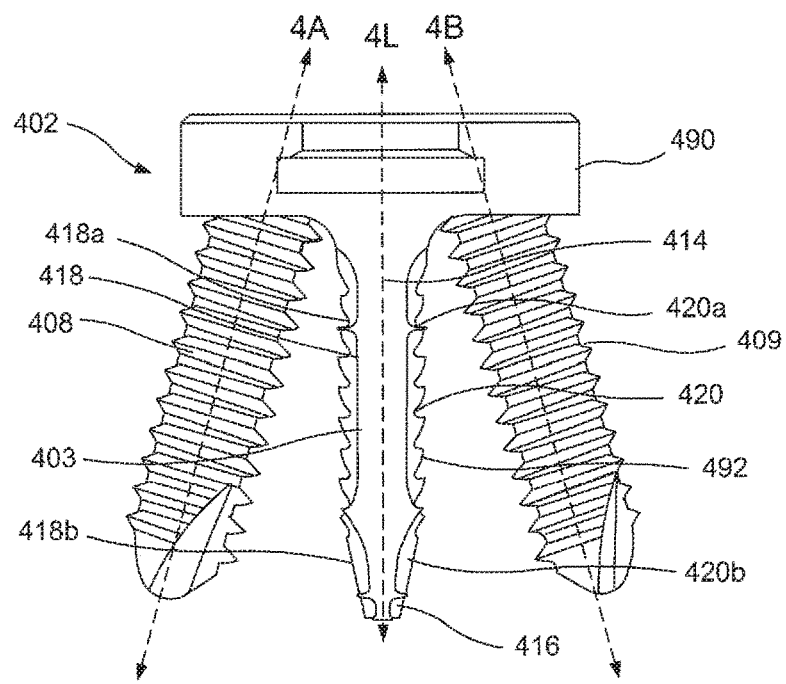
FIG. 22 shows a side view of an implant of the implant of FIG. 21.
Figure 23:
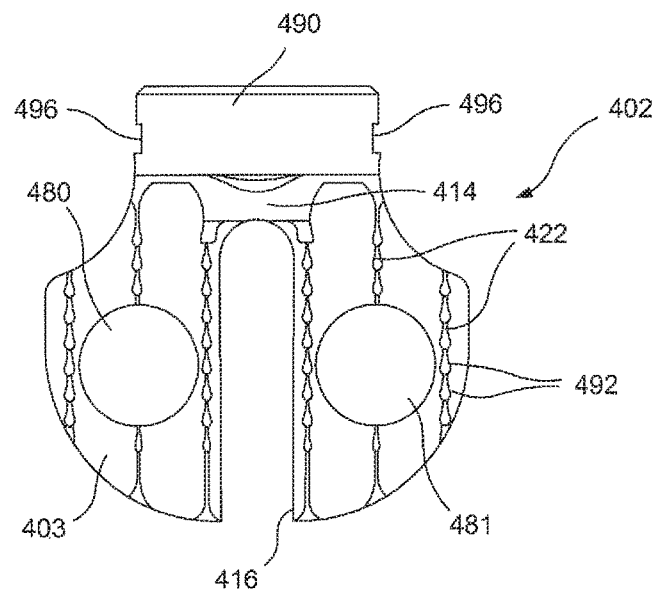
FIG. 23 shows another side view of the implant of FIG. 21.
Figures 24, 25:
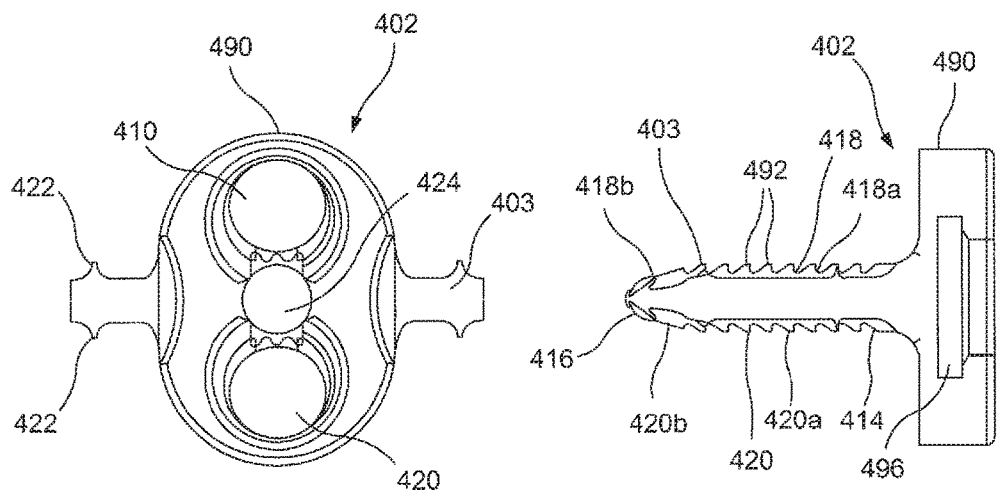
FIG. 24 shows a top plan view of the implant of FIG. 21.
FIG. 25 shows yet another side view of the implant of FIG. 21.

The implants 102, 202 have been described as wedge-shaped. However, as those skilled in the art will understand, other implant shapes are possible. For example, as shown in FIG. 19 an implant 302 is similar to the implants 102, 202, with a first end 314 and a second end 316 along a longitudinal axis, and first and second surfaces 318, 320, respectively. The implant 302 is used substantially the same the manner described for implant 202. In contrast to the implants 102, 202, the surfaces 318, 320 define a more pronounced transition from a second end 316 to a first end 314 along the longitudinal axis. When compared with the gradual opening of the facet joint due to the wedge shape of the exemplary implants 102, 202, the opening of the facet joint with the implant 302 is more abrupt.

The relatively abrupt transition is provided by a shape of the implant 302 defined by the first and second surfaces 318, 320 and an insertion surface at the second end 316 that connects the first and second surfaces 318, 320. Each of the first and second surfaces 318, 320 has first regions 318a, 320a, respectively, and second regions 318b, 320b, respectively. The portions of the surfaces 318, 320 in the first regions 318a, 320a are substantially planar and substantially parallel to each other. In the second regions 318b, 320b, the first and second surfaces 318, 320 are shaped to provide a smooth insertion transition in an insertion direction from the second end 316 to the first end 314. The smooth transition may be provided by portions of the surfaces 318, 320 in the second regions 318b, 320b defining curved or planar surfaces that widen from the second end 316 in a direction toward the first regions 318a, 320a.

The insertion surface defined at the second end 316 is, in normal use, the first part of the implant 302 that contacts the facet joint during insertion. The insertion surface provides the initial opening of the facet joint. To provide the relatively abrupt opening, the insertion surface could be described as having a blunt profile. The blunt profile may be defined by an insertion surface which is planar, arced, bullet-shaped, and other surface shapes as those skilled in the art would understand. In comparison with insertion surfaces of second ends 116, 216 of the other exemplary implants 102, 202, the insertion surface of the second end 316 is relatively wider to provide a more abrupt opening. Since the inferior and superior surfaces of facet joint are substantially parallel to one another the parallel planar portions 318a, 320b of the surfaces 318, 320 fit well anatomically to the facet joint.

Figure 33:
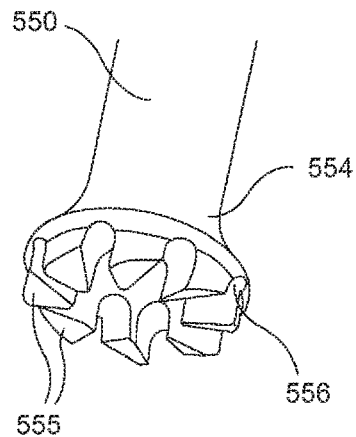
FIG. 33 shows an enlarged perspective view of a distal end of the reamer of FIG. 31.
Figure 34:
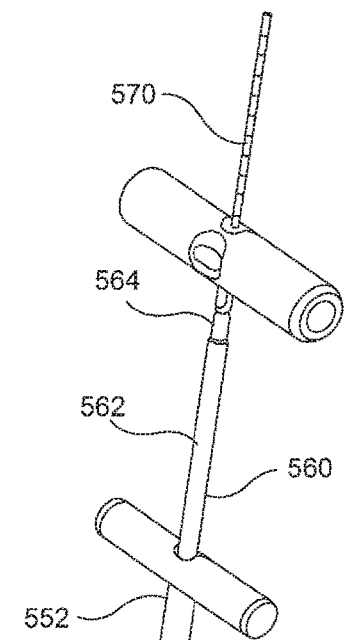
FIG. 34 shows a perspective view of a curette and reamer according to the system of FIG. 20.
Figure 35:
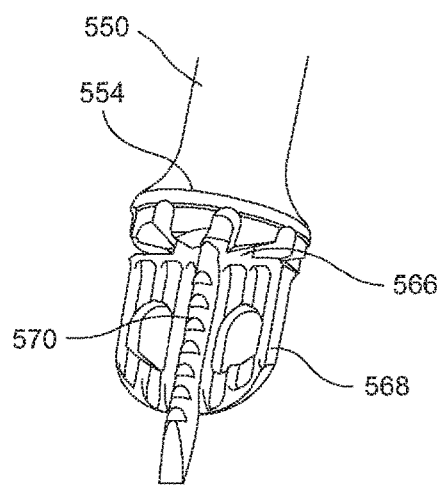
FIG. 35 shows an enlarged perspective view of a distal portion of the curette and reamer of FIG. 34.

As shown in FIGS. 20-35, system 400 according to another exemplary embodiment of the present invention comprises an implant 402 and an implant holder 406. The implant 402 may be substantially similar to the implant 302, described above, comprising a body 403 sized and shaped for insertion into a facet joint and extending from a first end 414 to a second end 416, and a head portion 490 attached to the first end 414. The system 400 may further comprise a facet joint finder 530, as shown in FIGS. 31-32, for locating the facet joint, a reamer 550, as shown in FIGS. 31 and 33, for removing soft tissue and creating a seating surface for the implant 402 and a curette 560, as shown in FIGS. 34-35, for removing cartilage from the facet joint to facilitate insertion of the implant 402 therein, as will be described in further detail below.

As shown in FIGS. 21-25, the implant 402 includes a central opening 424 extending through the head portion 490 and the body 403 along a longitudinal axis 4L to accommodate a guide wire therethrough along with first and second openings 410, 412 extending through the head portion 490 to receive bone fixation elements 408, 409 therethrough. The first opening 410 extends along a first axis 4A, which is angled with respect to the longitudinal axis 4L, such that a first bone fixation element 408 be inserted through the first opening 410 extends along the first axis 4A which, when the implant 402 is in a desired position will aim the first bone fixation element 408 along a desired path into a first vertebra of a facet joint. The second opening 412 extends along a second axis 4B angled with respect to the longitudinal axis 4L in a second direction opposite the first axis 4A such that, when the implant 402 is in the desired position, a second bone fixation element 409 inserted through the second opening 412 extends along the second axis 4B into a second vertebra along a desired path. The angle between the first axis 4A and the longitudinal axis 4L and the angle between the first axis 4B and the longitudinal axis 4L in this embodiment are substantially equal to one another such that the implant 402 is substantially symmetrical with respect to the longitudinal axis 4L. The implant holder 406 is used to insert the implant 402 into the facet joint and guide the bone fixation elements 408, 409 into the first and second openings 410, 412, respectively. The head portion 490 of the implant 402 according to this embodiment also includes a recess 496 along opposing portions of a periphery thereof for engaging a portion of the implant holder 406.

Similarly to the implant 402, a shape of the body 403 transitions from the first end 414 to the second end 416 and is defined by first and second surfaces 418, 420 thereof. In particular, as described above in regard to the implant 302, each of the first and second surfaces 418, 420 has first regions 418a, 418b, respectively, and second regions 420a, 420b, respectively. The first regions 418a, 420a are substantially planar and parallel to one another while the second regions 418b, 420b taper toward the second end 416 to provide a smooth insertion transition. The body 403 also includes a plurality of ribs 422 projecting from each of the first and second surfaces 418, 420 to guide the implant 402 into the facet joint and facilitate engagement with the first and second vertebra. The ribs 422 extend along the surfaces 418, 420 from the first end 414 to the second end 416. The ribs 422, however, further include teeth 492 or a jagged edge extending therealong to enhance a grip between the implant and the surrounding tissue to prevent the implant 402 from being inadvertently pulled out of a facet joint into which it has been inserted. As would be understood by those skilled in the art, the teeth 492 are angled with peaks 494 thereof pointing toward the first end 414 to increase a pull-out resistance of the implant 402.

In addition, rather than a plurality of smaller holes extending through the body 403 to promote bone in-growth, as shown and described in regard to the implants 102-302, the implant 402 includes larger first and second holes 480, 481 extending through the body 403. The first hole 480 extends through a first portion of the body 403 from the first surface 418 to the second surface 420 on a first side of the central opening 424. The second hole 481 extends through a second portion of the body 403 from the first surface 418 to the second surface 420 on a second side of the central opening 424 opposite the first side. The first and second holes 480, 481 are sized and shaped to permit the holes 480, 481 to be filled with bone graft material to promote bone growth during the implantation process.

Figure 26:
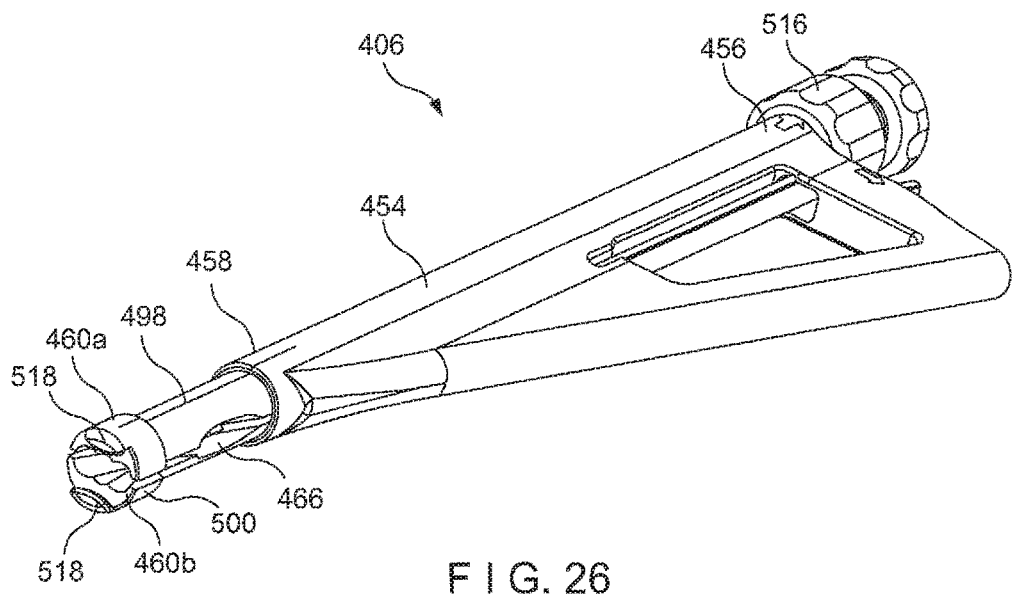
FIG. 26 shows a perspective view of an implant holder of the system of FIG. 20, in an implant receiving configuration.
Figure 27:
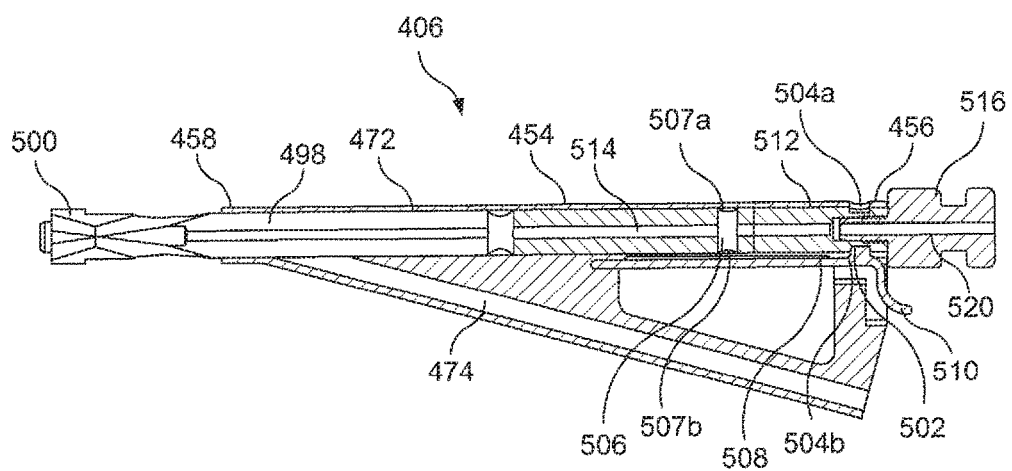
FIG. 27 shows a longitudinal cross-sectional view of the implant holder of FIG. 26, in the implant receiving configuration.
Figure 28:
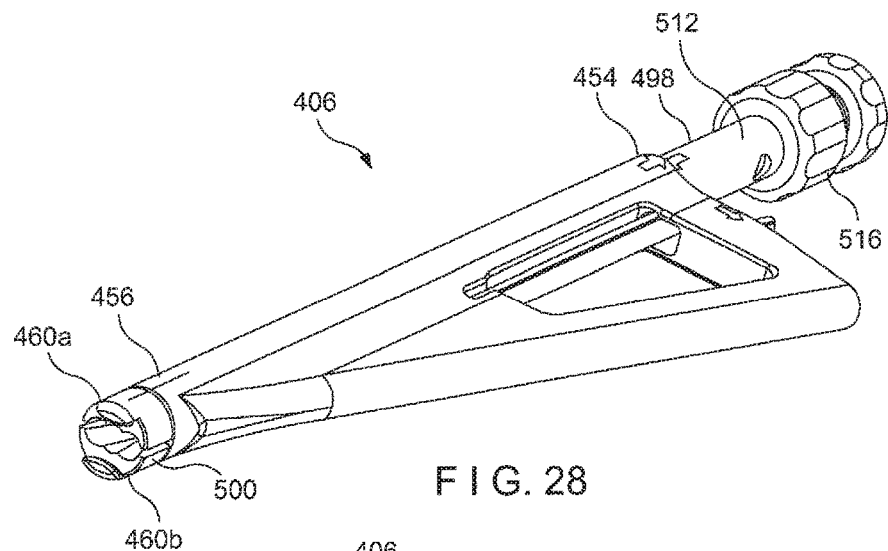
FIG. 28 shows a perspective view of the implant holder of FIG. 26, in a closed configuration.
Figure 29:
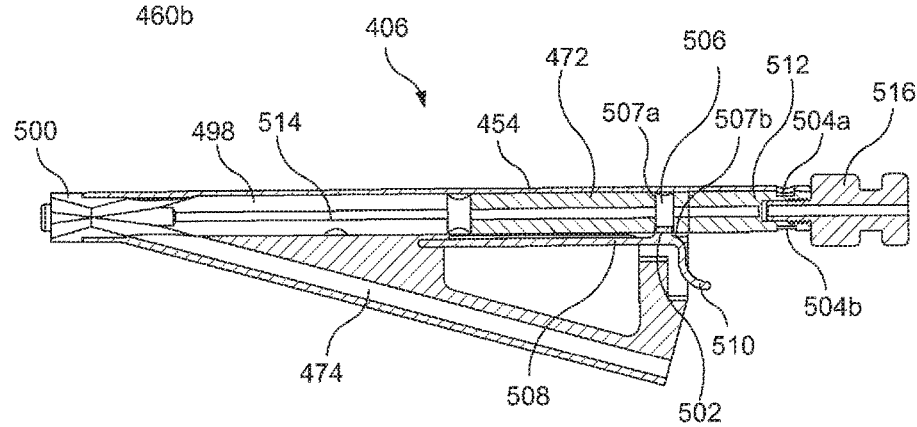
FIG. 29 shows a longitudinal cross-sectional view of the implant holder of FIG. 26, in the closed configuration.

As shown in FIGS. 26-30, the implant holder 406 includes a guide body 454 including a central channel 472 extending from a proximal end 456 to a distal end 458 and a shaft 498 slidably received within the central channel 472. The shaft 498 extends along a longitudinal axis to a distal end 500 which is configured to engage the head portion 490 of the implant 402. In particular the distal end 500 includes jaw members 460a, 460b extending distally therefrom on opposing sides of the shaft 498. The jaw members 460a, 460b are biased away from one another such that the head portion 490 may be received therebetween. The guide body 454 is slidable over the shaft 498 between an implant receiving configuration, as shown in FIGS. 26 and 27, in which the jaw members 460a, 460b receive the head portion 490 therebetween and a closed configuration, as shown in FIGS. 28 and 29, in which the jaw members 460a, 460b are moved toward one another to engage the recesses 496 to hold the implant 402 therebetween.

The guide body 454 includes a central channel 472 sized and shaped to slidably house the shaft 498 therein and a guide channel 474 extending through the guide body 454 at an angle relative to the central channel 472. The central channel 472 extends through the guide body 454 along a path oriented so that, when the shaft 498 engages the implant 402, the central channel 472 is aligned with the longitudinal axis 4L of central opening 424. The guide channel 474 extends through the guide body 472 such that when the shaft 498 engages the implant 402, the guide channel 474 is aligned with one of the first and second axes 4A, 4B of the first and second openings 410, 412, respectively. The guide body 454 is thus rotatable about the shaft 498 so that, when coupled to the implant 402, the guide channel 474 may be moved between a first hole configuration in which the guide channel 474 is aligned with the first opening 410 and a second hole configuration in which the guide channel 474 is aligned with the second opening 412. The guide body 454 also includes a locking mechanism 508 including a locking tab 502 biased toward a center of the central channel 472 to engage portions of the shaft 498 to fix the guide body 454 relative to the shaft 498 in one of the implant receiving or closed configuration and/or the first hole and second hole configurations. The locking mechanism 508 also includes a release lever 510 which may be used to draw the locking tab 502 out of engagement with the portions of the shaft 498 as will be described in further detail below.

Figure 30:
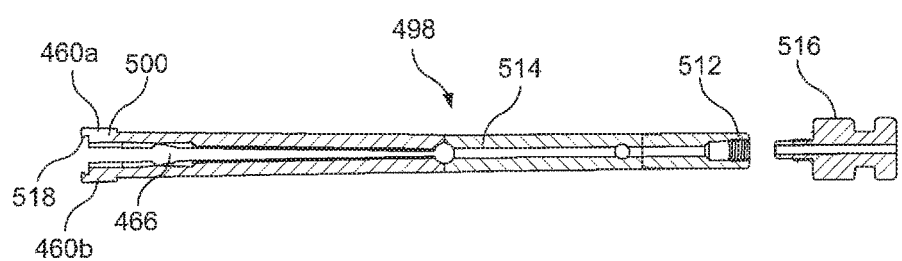
FIG. 30 shows a longitudinal cross-sectional view of a shaft of the implant holder of FIG. 26.
Figures 31, 32:
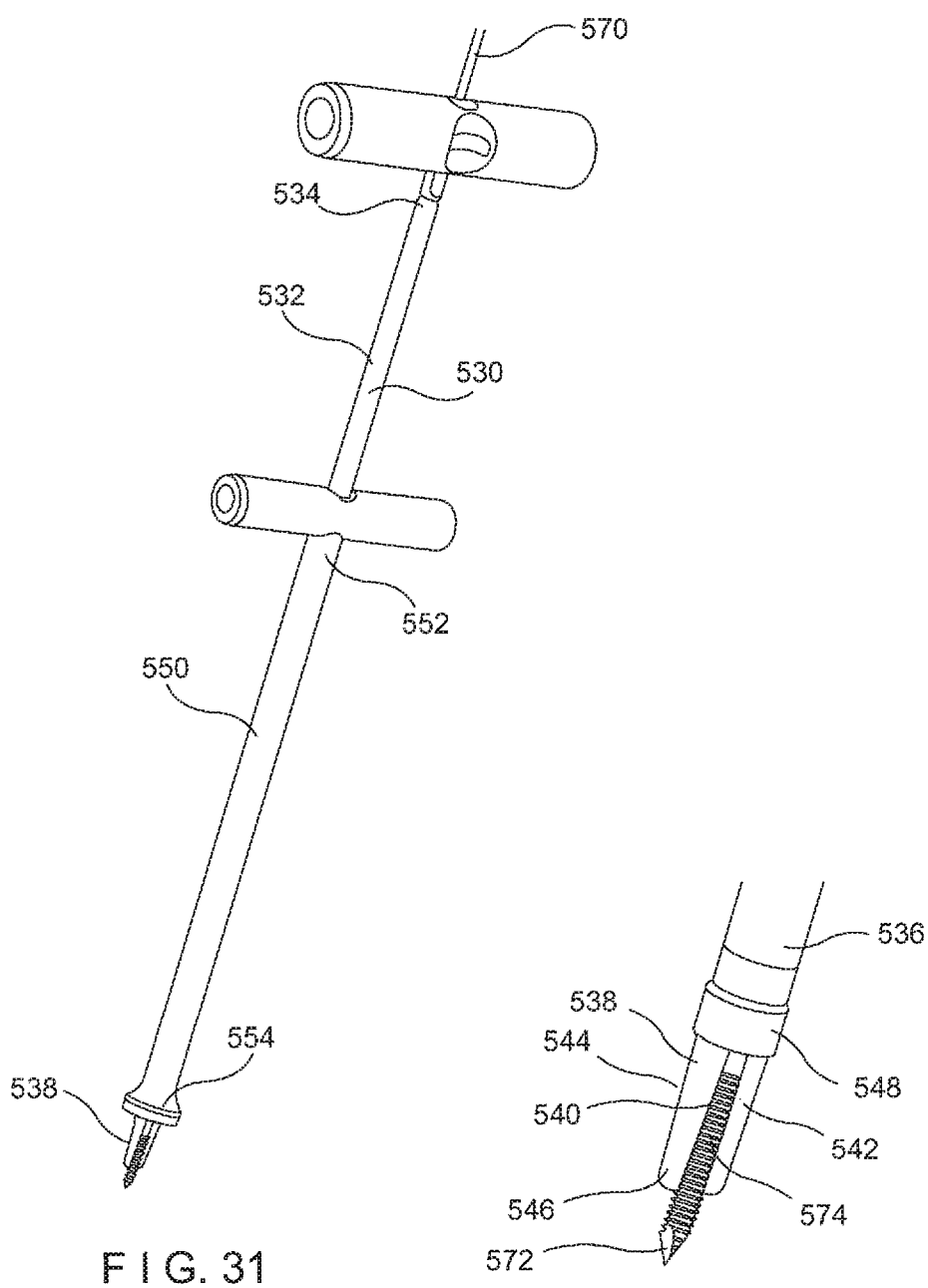
FIG. 31 shows a perspective view of a joint finding tool and a reamer according to the system of FIG. 20.
FIG. 32 shows an enlarged perspective view of a distal end of the joint finding tool of FIG. 31.

The shaft 498, as shown in FIG. 30, extends longitudinally from a proximal end 512 to the distal end 500 and includes a lumen 514 extending therethrough. The lumen 514 is sized and shaped to permit the implant holder 406 to be slid over a guide wire to insert the implant 402 into the facet joint. The proximal end 512 is configured to be coupled to an end cap 516 which may be used to hold the shaft 498 while the body 454 is moved between the implant receiving and closed configurations. The end cap 516 also includes a corresponding lumen 520 such that the guidewire may extend through both the end cap 516 and the shaft 498. As described above, the distal end 500 includes jaw members 460a, 460b for engaging the head portion 490 of the implant. The jaw members 460a, 460b may be formed via, for example, a slot 466 extending along a length of a distal portion of the shaft 498. The jaw members 460a, 460b may further include protrusions 518 extending radially inward from a portion thereof, the protrusions 518 sized and shaped to correspond to the recesses 496 in the head portion 490 of the implant 402.

The shaft 498 includes first and second locking recesses 504a, 504b extending along a proximal portion of the shaft 498 for engaging the locking tab 502 to lock the implant holder 406 in the implant receiving configuration. The first and second locking recesses 504a, 504b in this embodiment are substantially diametrically opposed from one another. The locking tab 502 may be received in either of the first and second locking recesses 504a, 504b to lock the implant holder 406 in the implant receiving configuration. The shaft 498 also includes a locking hole 506 extending laterally therethrough distally of the first and second locking recesses 504a, 504b. The locking hole 506 is sized and shaped to engage the locking tab 502 to lock the implant holder 406 in the closed configuration and one of the first and second hole receiving configurations. The locking hole 506 extends entirely through the shaft 498 from a first opening 507a to a second opening 507b substantially opposing the first opening 507a. The first opening 507a may be longitudinally aligned with the first locking recess 504a while the second opening 507b is longitudinally aligned with the second locking recess 504b. The locking hole 506 is positioned distally of the first and second locking recesses 504a, 504b such that when the locking tab 502 engages the second locking hole 506, the implant holder 406 is locked in the closed configuration. Thus, in the implant receiving configuration, the distal end 500 of the shaft 498 may be positioned over the head portion 490 of the implant 402. Once the head portion 490 has been positioned between the jaw members 460a, 460b, as desired, a user moves the release lever 510 to disengage the locking tab 502 from the first locking hole 504 and slides the guide body 454 distally over the jaw members 460a, 460b until the implant holder 406 is in the closed configuration and the locking tab 502 engages the second locking hole 506. In the closed configuration, the guide body 454 is moved longitudinally over the jaw members 460a, 460b such that the protrusions 518 engage the recesses 496 of the head portion 490.

The distal portion of the shaft 498 also includes a first guide channel 522 and a second guide channel 524 extending therethrough. The first guide channel 522 extends through the distal portion of the shaft 498 at an angle relative to the longitudinal axis of the shaft 498 corresponding to an angle between the first axis 4A of the first opening 410 and the longitudinal axis 4L of the implant 402. The second guide channel 524 extends through the distal portion of the shaft 498 at an angle relative to the longitudinal axis of the shaft 498 corresponding to an angle between the second axis 4B of the second opening 412 and the longitudinal axis 4L of the implant 402. When the implant holder 406 is in the closed configuration, the guide channel 474 of the body 454 is aligned with one of the first and second guide channels 522, 524 of the shaft 498 such that one of the bone fixation elements 408, 409 may be guided therethrough into one of the first and second openings 410, 412 of the implant 402. In particular, when the locking tab 502 engages the first opening 507a of the locking hole 506, the implant holder 406 is locked in the first hole configuration such that the guide channel 474 is aligned with the first guide channel 522 of the shaft 498. When the locking tab 502 engaging the second opening 507b of the locking hole 506, the implant holder 406 is locked in the second hole configuration such that the guide channel 474 is aligned with the second guide channel 524 of the shaft 498. As discussed above, the implant holder 406 may be moved between the first and second hole configurations by pulling the release lever 510 to disengage the locking tab 502 from one of the first and second openings 507a, 507b of the locking hole 506 and rotating the guide body 454 about the shaft 498 until the locking tab 502 engages the other of the first and second openings 507a, 507b.

As shown in FIGS. 31 and 32, the facet joint finder 530 includes a shaft 532 extending longitudinally from a proximal end 534 to a distal end 536 attached to a joint finding tip 538 and a lumen extending therethrough to receive a guidewire therein. The joint finding tip 538 is sized and shaped to be inserted into a facet joint of a patient and includes first and second planar surfaces 542, 544 which taper toward one another to a distal end 546 thereof to facilitate insertion into the facet joint. A length of the joint finding tip 538 is selected to correspond to a length of the implant 402. The joint finding tip may also include a longitudinal slot 540 extending therealong to accommodate a guidewire that is wider than a distance between the first and second planar surfaces 542, 544. The facet joint finder 530 may also include a stop 548 extending radially outward from a portion of the shaft 532 immediately proximal the joint finding tip 538. The stop 548 prevents a reamer 550 which may be used in conjunction with the facet joint finder 530 from extending distally past the stop 548.

As shown in FIGS. 31 and 33, the reamer 550 extends longitudinally from a proximal end 552 to a distal end 554 and includes extending therethrough a lumen sized and shaped to receive the shaft 532 of the facet joint finder 530. The distal end 554 of the reamer 550 has, for example, a substantially circular distal face 556 including blades 558 extending therealong for removing soft tissue and creating a seating surface for receiving the head portion 490 of the implant 402.

As shown in FIGS. 34 and 35, the curette 560 includes a shaft 562 extending longitudinally from a proximal end 564 to a distal end 566 attached to an implant-shaped tip 568 and a lumen extending therethrough to accommodate a guide-wire therein. As shown, the curette 560 may also be used in conjunction with the reamer 550 described above. Thus, the shaft 562 is sized and shaped to be slidably received within the lumen of the reamer 550. The implant-shaped tip 568 has a size and shape corresponding to the body 403 of the implant 402 to be inserted into the facet joint such that that the tip 568, when inserted into the facet joint, removes cartilage therefrom to accommodate insertion of the implant 402 therein. The curette 560 may also include a stop (not shown) extending radially outward from a portion of the shaft 562 proximal of the implant-shaped tip 568 such that when the curette is coupled with the reamer 550, the reamer 550 is prevented from moving distally past the stop.

Figure 36:
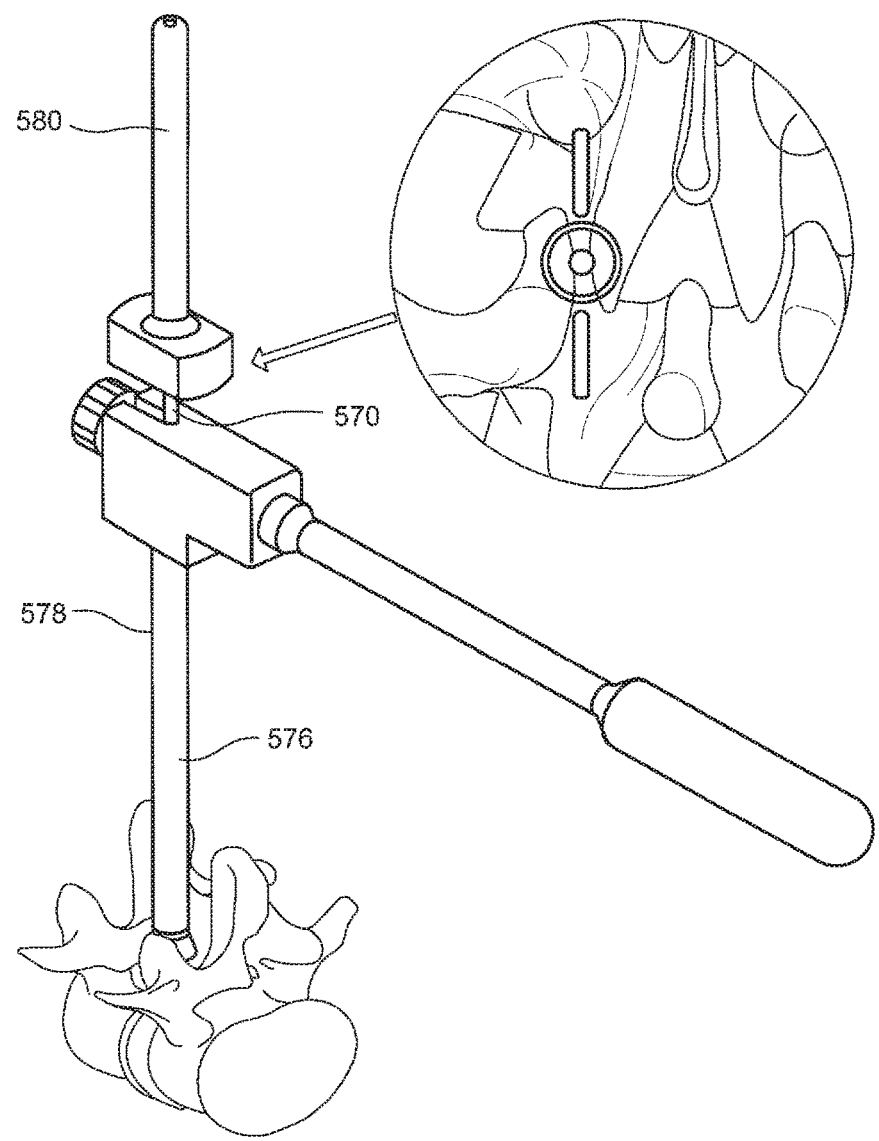
FIG. 36 shows a perspective view of a guide wire inserted into a joint via an aiming guide according to an exemplary surgical method of the present invention.
Figures 37, 38:
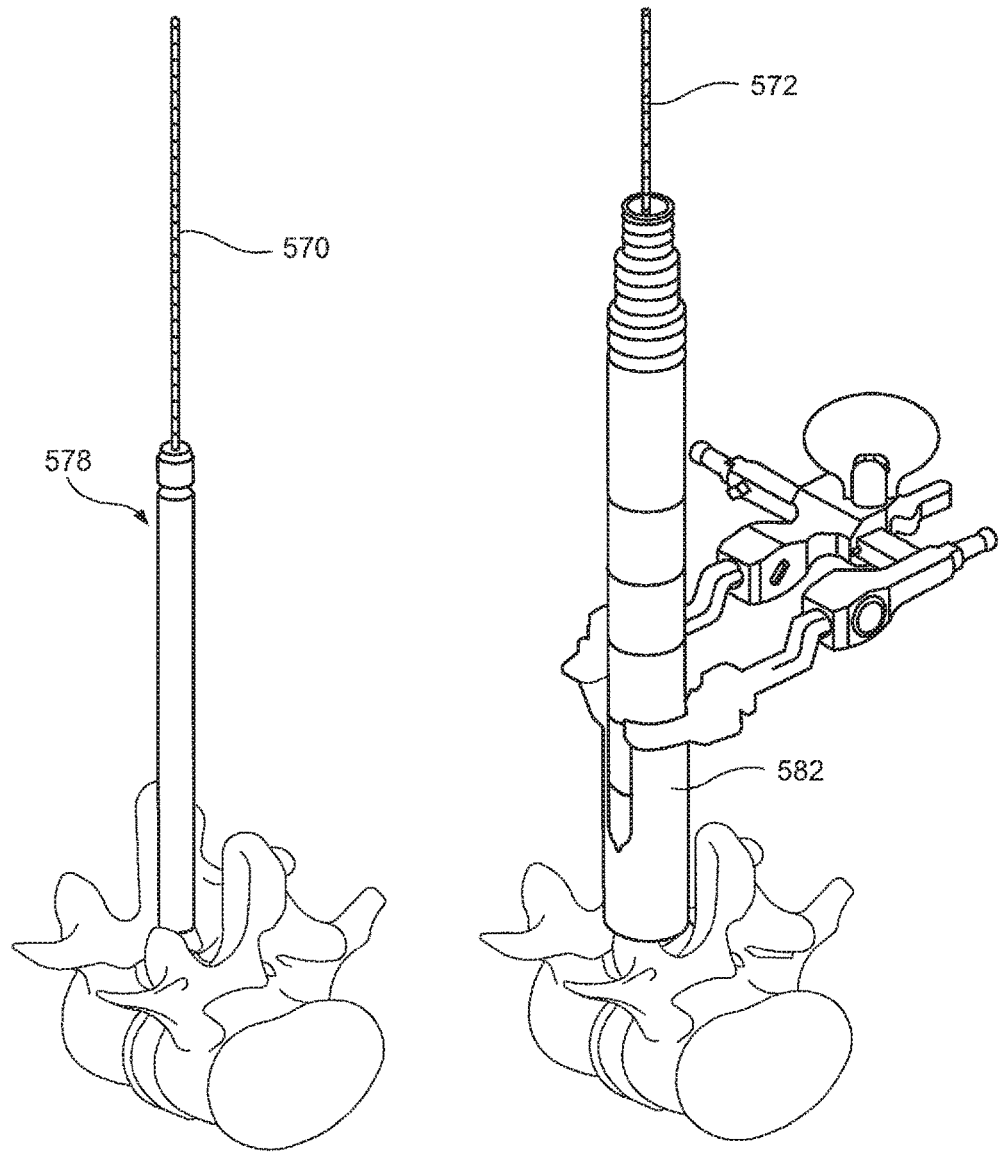
FIG. 37 shows a perspective view of a guide wire and shaft of the aiming guide of FIG. 36.
FIG. 38 shows a perspective view of a soft tissue retractor over the guide wire and aiming guide of FIG. 37.

FIGS. 36-43 show an exemplary surgical technique using the system 400. The surgical technique comprises inserting a guide wire 570 into the facet joint. In this exemplary embodiment, the guide wire 570 extends longitudinally to a distal end including a flat tip 572 and threads 574, as shown in FIG. 32, or teeth, as shown in FIG. 35, extending along a length of the guide wire 570 distally of the flat tip 572 to facilitate holding within the bone. In one exemplary embodiment, as shown in FIG. 36, the guide wire 570 is inserted into the joint using an aiming guide 576 including x-ray markers enabling visualization of the implant placement within the facet joint. The x-ray markers may include, for example, pins to indicate a width of the implant 402 to be inserted and a ring to show a size of the head portion 490. Once the x-ray markers indicate proper positioning, the distal end 572 the guide wire 570 is inserted through an aiming shaft 578 thereof and into the facet joint. As would be understood by those skilled in the art, a tamp 580 may be attached to the proximal end of the guide wire 570 to prevent the guide wire 570 from being inserted more than a desired distance (e.g., 15 mm) into the facet joint to prevent damage of neural structures. Once the guide wire has been inserted into the facet joint, an aiming handle may be removed from the aiming guide 576, as shown in FIG. 37, so that only the aiming shaft 578 remains about the guide wire 570. As shown in FIG. 38, a soft-tissue retractor 582 is then slid over the guide wire 570 and/or aiming shaft 578 to remove soft tissue surrounding the area in which the implant 402 is to be inserted.

Figure 39:
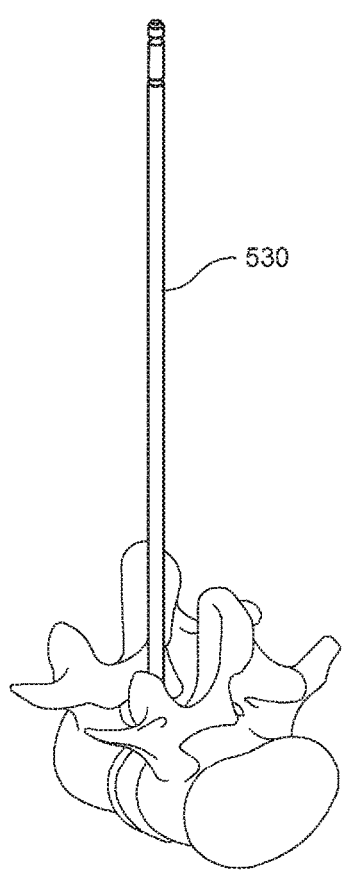
FIG. 39 shows a perspective view of a guide wire inserted into a joint via a joint finding tool according to an alternate embodiment of the method of FIG. 36.
Figure 40:
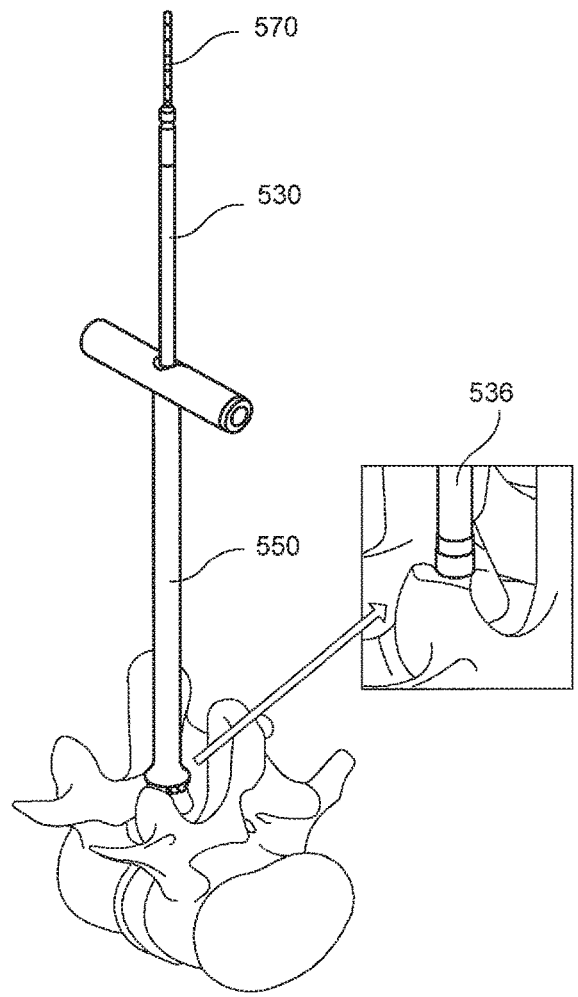
FIG. 40 shows a perspective view of a reamer slid over the joint finding tool of FIG. 39.

According to another exemplary embodiment, as shown in FIG. 39, the guide wire 570 is placed within the facet joint via the facet joint finder 530. The joint finding tip 538 is inserted into the facet joint in which the implant 402 is to be inserted. Once positioned in the facet joint, the guide wire 570 is inserted through the shaft 532 of the facet joint finder 530 until the distal end 572 of the guide wire 570 is inserted into the facet joint. As described above, the distal end 572 should not be inserted more than a desired distance (e.g., 15 mm) into the joint to prevent damage to the neural structures. Once the guide wire 570 has been placed, as shown in FIG. 40, the reamer 550 is slid over the shaft 532 of the facet joint finder 530 until a distal end of the reamer 550 contacts the stop 548. The distal face 556 of the reamer 550 is used to create a surface for implant seating. The reamer 550 and the facet joint finder 530 may then be removed, leaving the guide wire 570 inserted in the facet joint. The soft tissue retractor 582 is then slid over the guide wire 570 to remove the soft tissue surrounding the implant area.

Once the guide wire 570 has been inserted into the facet joint and soft tissue has been removed using either of the methods described above, the curette 560 is slid over the guide wire 570 until the implant-shaped tip 568 is inserted into the facet joint to remove the cartilage in the facet joint, creating optimal conditions for bony fusion. If the surrounding bone has not been reamed already during the guide wire 570 placement, the reamer 550 may be slid over the shaft 562 of the curette 560 so that the distal face 556 may create a surface for implant seating. Once the cartilage has been removed, the curette 560 and/or the reamer 550 may be removed, leaving the guide-wire 570 inserted in the facet joint.

Figure 41:
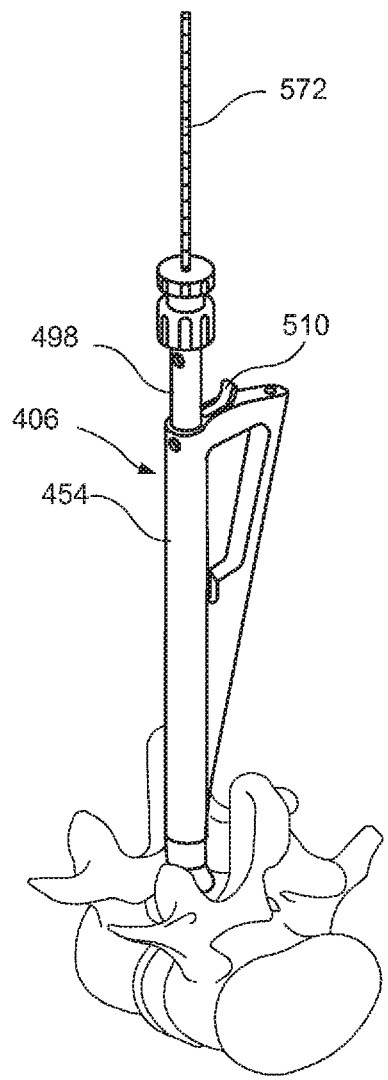
FIG. 41 shows a perspective view of an implant holder inserting an implant into the joint according to the method of FIG. 36.

The user may then pack the first and second holes 480, 481 of the implant 402 with bone graft material. Once the holes 480, 481 have been filled with bone graft material, the implant 402 may be coupled to the implant holder 406. In particular, the implant holder 406, in the implant receiving configuration, is positioned over the implant 402 such that the head portion 490 of the implant 402 is received between jaw members 460a, 460b of the shaft 498. As discussed above, the implant holder 406 may be locked in the implant receiving configuration via the locking mechanism 508. Once the implant holder 406 is positioned over the implant 402 as desired, however, the user pulls the release lever 510 of the locking mechanism 508, to slide the body 454 of the implant holder 406 distally over the shaft 498 until the implant holder is locked in the closed configuration and the head portion 490 of the implant 402 is gripped between the jaw members 460a, 460b, as shown in FIG. 41. Using the implant holder 406, the implant 402 is then inserted into the facet joint by sliding the implant holder 406 over the guide wire 507. Upon insertion of the implant 402 into the facet joint, the guide wire may be removed.

Figure 42:
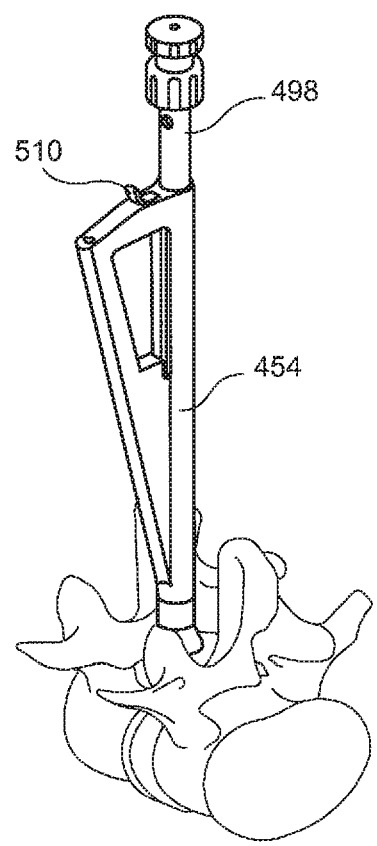
FIG. 42 shows a perspective view of a body of the implant holder rotated about a shaft thereof according to the method of FIG. 36.

As described above, the central channel 472 of the body 454 and the shaft 498 received therein are aligned with the longitudinal axis 4L of the central opening 424 of the implant 402 while the guide channel 474 of the implant holder 406 is aligned with one of the first and second axes 4A, 4B of the first and second openings 410, 412. In situations in which the guide channel 474 is aligned with the first opening 410 (i.e., the locking tab 502 of the locking mechanism 508 engages the first opening 507a of the locking hole 506 in the shaft 498), an awl may be inserted through the guide channel 474 and into the first opening 410 along the first axis 4A to create a hole in the first vertebra of the facet joint. The bone fixation element 408 may then be inserted through the guide channel 474 and into the first opening 410 such that a shaft thereof extends into the hole formed in the first vertebra and a head thereof engages a threading extending along an interior of the first opening 410. The user then pulls the release lever 510 of the lock mechanism 508 to disengage the locking tab 502 from the first opening 507a of the locking hole 506 such that the body 454 of the implant holder 406 may be rotated around the shaft 498, as shown in FIG. 42, until the locking tab 502 engages the second opening 507b of the locking hole 506, aligning the guide channel 474 with the second opening 412 of the implant 402.

Figure 43:
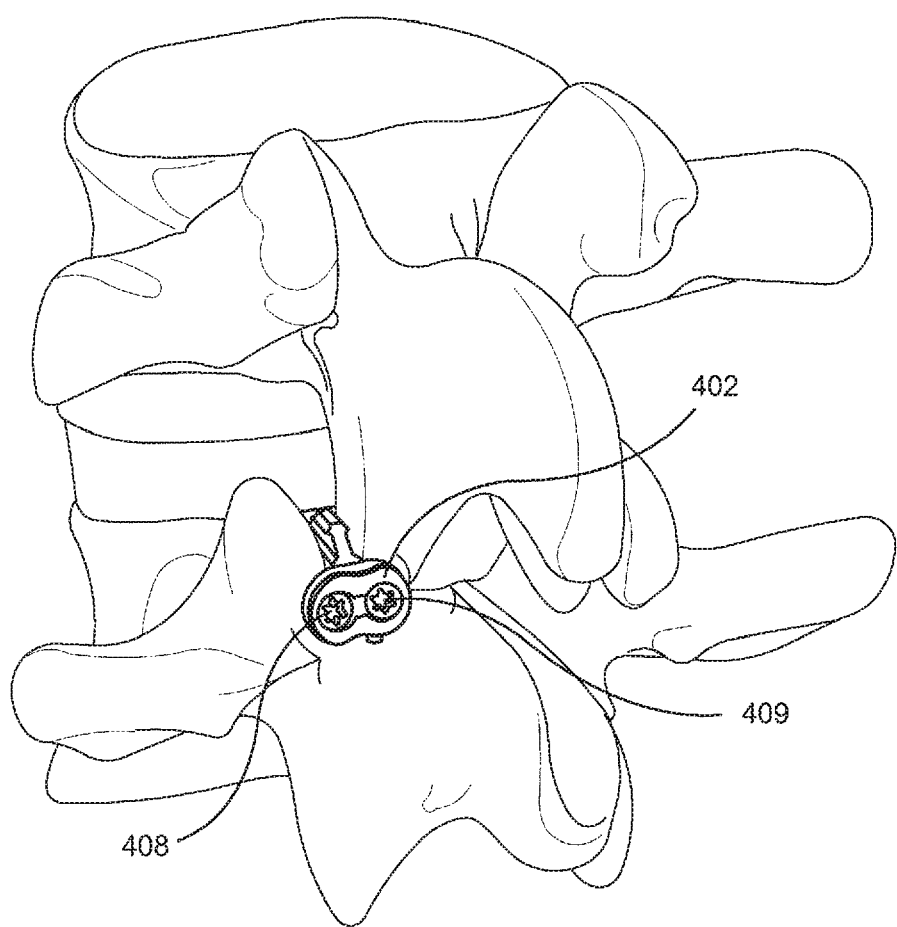
FIG. 43 shows a perspective view of the implant implanted in the joint according to the method of FIG. 36.

Similarly to the first opening 410, an awl may be used to form a hole in the second vertebra of the facet joint via the guide channel 474 and the second bone fixation element 409 may be inserted therethrough such that a shaft thereof extends into the second vertebra and a head thereof engages a threading extending along an interior of the second opening 412. Although the exemplary embodiment specifically describes a situation in which the guide channel 474 is initially aligned with the first opening 410 of the implant 402, it will be understood by those of skill in the art that the guide channel 474 may initially be aligned with the second opening 412 such that the bone fixation element 409 is inserted through the second opening 412 and into the second vertebra prior to insertion of the bone fixation element 408 through the first opening 410 and the first vertebra. Once the first and second bone fixation elements 408, 409 have been inserted through the first and second openings 410, 412, respectively, the implant holder 406 may be disengaged from the implant 402 and removed from the body, as shown in FIG. 43. The implant holder 406 may be removed by pulling the release lever 510 to move the implant holder to the implant receiving configuration to disengage the implant 402. Alternatively, the implant holder 406 may be disassembled by removing the end cap 516 from the proximal end 512 of the shaft 498 so that the body 454 may be slidably removed from the shaft 498. Once the body 454 has been removed, the jaw members 460a, 460b of the shaft 498 revert to their biased, open configuration such that the implant 402 is released from therebetween. Proper positioning of the implant 402 and the bone fixation elements 408, 409 may be ensured by visually inspecting the implant 402 and/or viewing x-ray images showing the positioning of the implant 402 in the facet joint.

Figure 44:
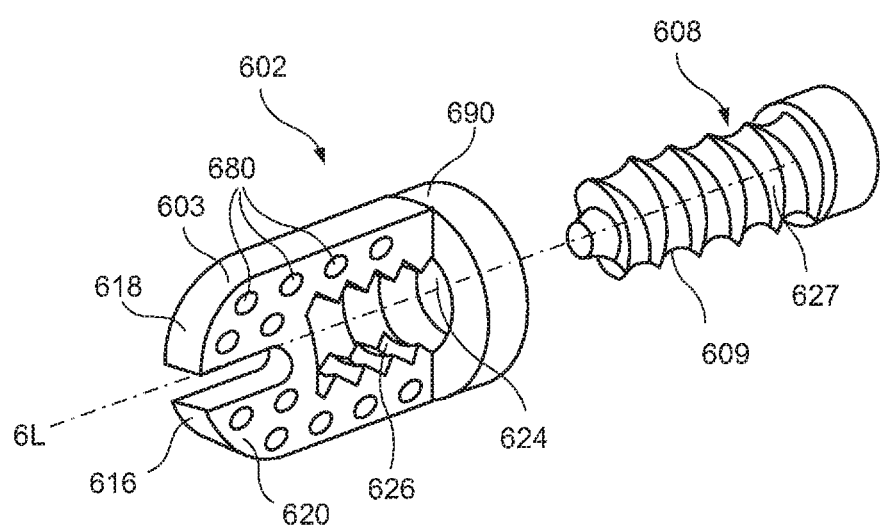
FIG. 44 shows a perspective view of an implant according to another exemplary embodiment of the present invention.
Figures 48, 49:
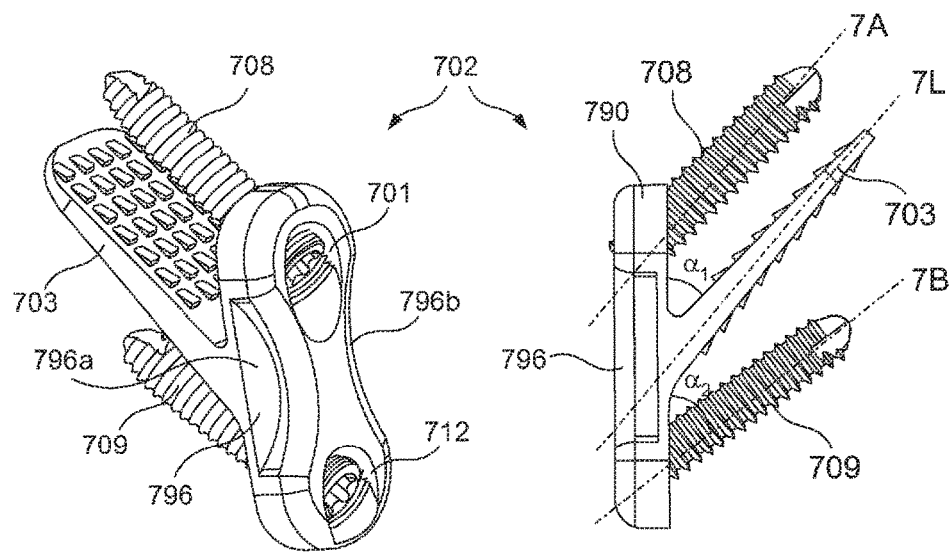
FIG. 48 shows a first perspective view of the implant of FIG. 45 with bone fixation elements inserted therethrough.
FIG. 49 shows a second perspective view of the implant of FIG. 48.
Figures 50, 51:
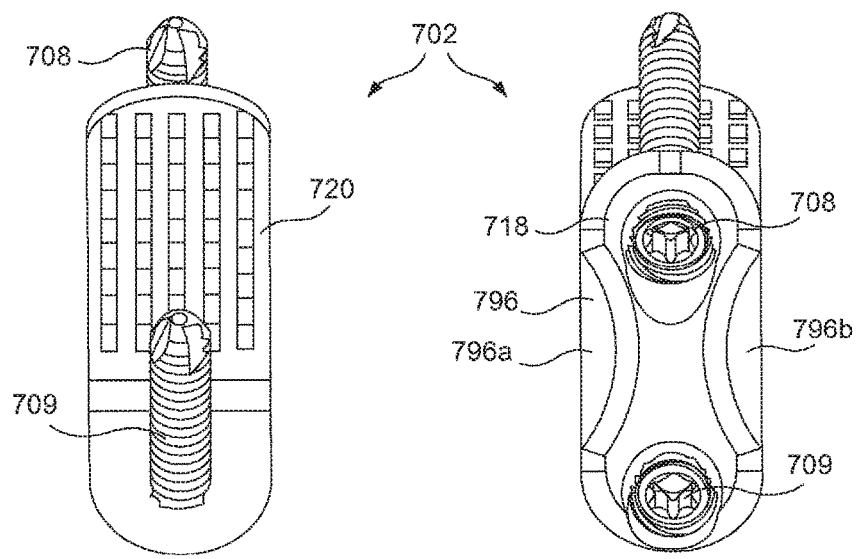
FIG. 50 shows a third perspective view of the implant of FIG. 48.
FIG. 51 shows a fourth perspective view of the implant of FIG. 48.

As shown in FIG. 44, an implant 602 may be substantially similar to the implants 202, 302 and 402, described above, comprising a body 603 extending distally from a head portion 690. The body 603 may be wedge-shaped, similarly to the implant 202. Alternatively, the body 603 may be substantially similar to the bodies 303, 403 including first and second planar surfaces 618, 620 having first portions 618a, 620a substantially parallel to one another and second portions 618b, 620b tapering toward one another to a distal end 616 thereof to facilitate insertion into a facet joint. The implant 602 includes a central opening 624 extending longitudinally through the head portion 690 and the body 603 along a longitudinal axis 6L. The implant 602, however, does not include first and second openings extending therethrough at an angle relative to the longitudinal axis 6L. Rather, a proximal portion of the central opening 624 is sized and shaped to receive a bone fixation element 608 therein. The proximal portion of the central opening 624 may include a threading 626 extending therealong to engage a threading 627 along a shaft 609 of the bone fixation element 608. A diameter of a shaft is larger than a distance between the first and second planar surfaces 618, 620 of the implant 602 such that the proximal portion of the central opening 624 is laterally open to an exterior thereof. Thus, the bone fixation element 608 may be inserted into along the longitudinal axis 6L into the central opening 624 to fix the implant 602 within the facet joint. In particular, the threads 627 along the shaft 609 will engage the surrounding bone to fix the implant 602 therein. Similarly to the head 290, the head 690 is of a larger width and may act as a stop for preventing the head portion 690 from being inserted into the facet joint. Similarly to the holes on the other embodiments that are for promoting bony fusion, for example, holes 180, 480, the body 603 also comprises a plurality of openings 680 extending therethrough from the first surface 618 to the second surface 620.

FIGS. 45-64 depict a system according to another embodiment of the invention including an implant 702 configured for use with an insertion instrument 802. As will be described in greater detail hereinafter, the exemplary system described hereafter is configured for use in cervical spine fixation procedures.

The exemplary implant 702 may be substantially similar to the implants 102, 202, described above. Similarly to the implant 102, the implant 702 has a body 703 extending distally from a head portion 790. The body 703 may be substantially wedge-shaped, tapering from a first end 714 to a second end 716 along a longitudinal axis 7L. The longitudinal axis 7L of the body 703 extends at a non-perpendicular angle from a plane housing the head portion 790. In an exemplary embodiment, an angle $\alpha_1$ between the head portion 790 and the longitudinal axis 7L is approximately 45°, although any other angle may be employed without deviating from the scope of the invention. For example, the angle $\alpha_1$ could be any angle between 30° to 90°. The body 703 may further comprise a plurality of ribs 722 projecting from each of first and second surfaces 718, 720 of the body 703 to facilitate engagement with first and second adjoining vertebra. The ribs 722 extend along the surfaces 718, 720 from the first end 714 to the second end 716. The ribs 422 further include teeth 792 or a jagged edge extending therealong to enhance a grip between the implant 702 and the surrounding tissue to prevent the implant 702 from being inadvertently pulled out of a cervical joint into which it has been inserted. As would be understood by those skilled in the art, the teeth 792 are angled with peaks 794 thereof pointing toward the first end 714 to increase a pull-out resistance of the implant 702. It is noted that although the exemplary embodiment is depicted with five columns of ribs 422, any number and orientation of the ribs 422 may be used without deviating from the scope of the invention. In an exemplary embodiment, a width of the head portion 790 may be approximately 8 mm, a height may be approximately 17.5 mm and a thickness may be approximately 2.2 mm, although any other measurements may be used without deviating from the scope of the invention. Furthermore, the second end 716 of the body 703 may be approximately 0.7 mm in thickness although any other measurement may be used to conform to the requirements of a particular procedure.

The implant 702 further includes first and second openings 710, 712 extending through the head portion 790 to receive bone fixation elements (e.g., bone screws) 708, 709 therethrough. The first opening 710 extends along a first axis 7A, which is substantially parallel to the longitudinal axis 4L, such that the first bone screw 708 inserted through the first opening 710 extends along the first axis 7A which, when the implant 702 is in a desired position aims the first bone screw 708 along a desired path into a first vertebra of a facet joint. The second opening 712 extends along a second axis 7B angled with respect to the plane housing the body 703 at an angle $\alpha_2$ greater than the angle $\alpha_1$. In an exemplary embodiment, the angle $\alpha_2$ may be approximately 55°, although any other angle may be used without deviating from the scope of the invention. As those skilled in the art will understand, the angular orientation of the longitudinal axes 7A and 7B are selected such that, when the implant 702 is in the desired position, first and second bone screws 708, 709 extend into first and second adjoining vertebrae along desired paths. The head portion 790 of the implant 702 may also include recesses 796 each having a slot 796a, 796b along opposing portions of a periphery thereof for engaging a portion of an implant holder 802, as described in greater detail with respect to earlier embodiments.

FIGS. 52-64 depict an exemplary implant holder 802 used to insert the implant 702 into the facet joint and guide the bone screws 708, 709 into the first and second openings 710, 712, respectively. The implant holder 802 is formed substantially similarly to the implant holder 406 but comprises a handle 804 on a proximal portion thereof to aid in handling and manipulation thereof. The implant holder 802 includes a guide body 806 extending along a longitudinal axis 8L from a proximal end 808 to a distal end 810. The guide body comprises a locking channel 812 extending longitudinally therethrough substantially aligned with the longitudinal axis 8L from a proximal end 814 to a distal end 816, which is proximate to the distal end 810 of the guide body 806. The body 806 further comprises the first screw channel 818 and a second screw channel 824 extending therethrough from respective proximal ends 820, 826 to respective distal ends 822, 828. In an exemplary embodiment, the first screw channel 818 extends at an angle to the longitudinal axis 8L such that a longitudinal axis 8A of the first screw channel 818 intersects a longitudinal axis 8B of the second screw channel 824.

Figure 52:
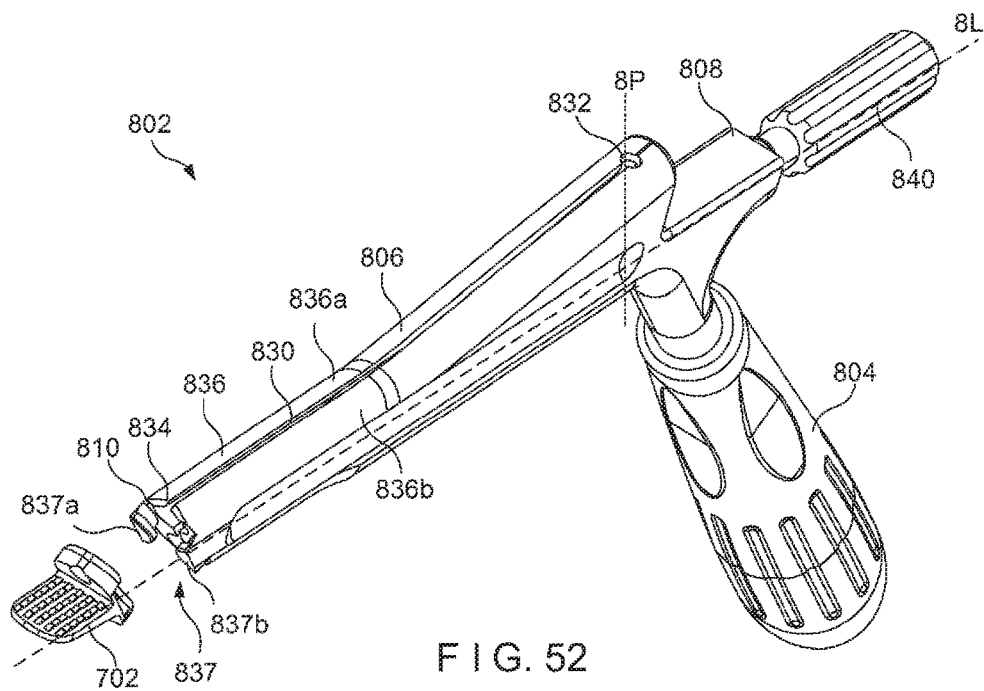
FIG. 52 shows a first perspective view of an insertion instrument used to guide the implant of FIG. 45 to a target position in the body.
Figure 53:
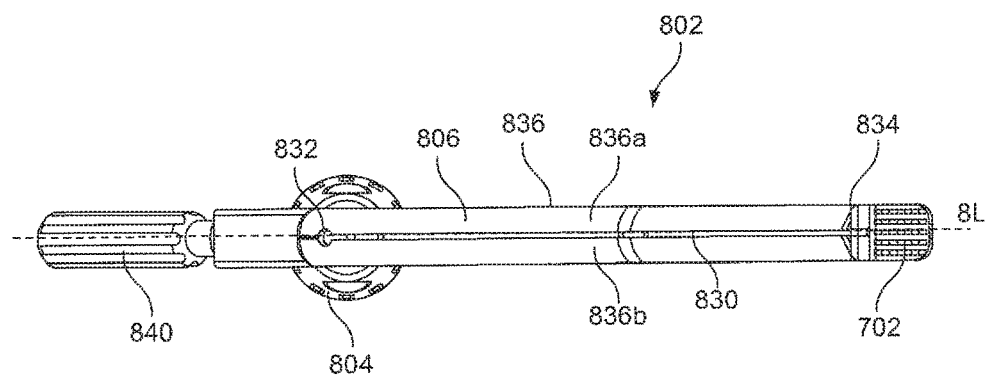
FIG. 53 shows a plan view of the insertion instrument of FIG. 52.

As shown more clearly in FIGS. 52-53, an upper surface of the body 806 comprises a longitudinal slot 830 extending from a proximal end having an increased width portion 832 to a distal end 834 open to the distal end 810 of the body 806. The slot 830 defines compliant arms 836 positioned on either side of the slot 830. First and second compliant arms 836a, 836b are pivotally moveable relative to each other about an axis 8P defined by the increased width portion 832. The first and second compliant arms 836a, 836b combine to form a jaw 837 at the distal end 834. The jaw 837 has a first jaw member 837a and a second jaw member 837b. In an operative configuration, the slot 830 is compressed to move the arms 836a, 836b toward one another and thereby move the jaw members 837a, 837b from a first size and dimension for insertion of the implant 702 into the jaw 837 to a second size and dimension for grasping and holding the implant 702 in the jaw 837.

Figure 54:
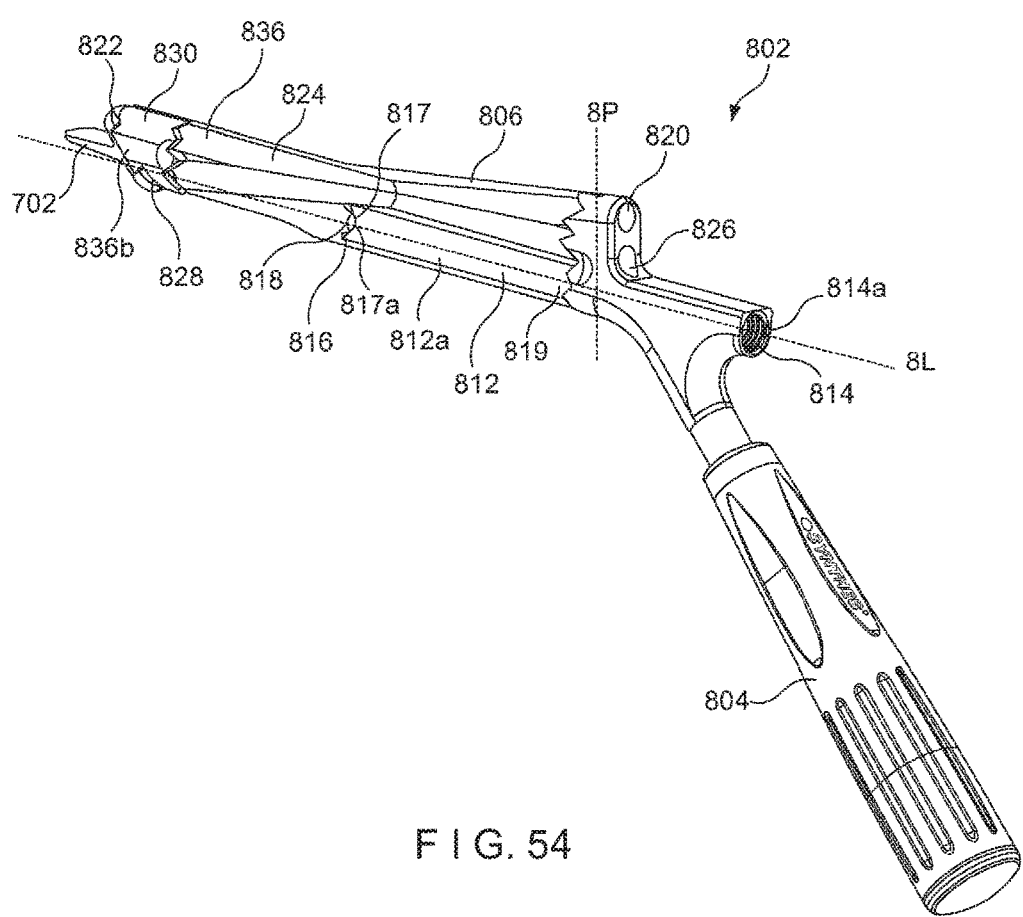
FIG. 54 shows a second perspective view of an insertion instrument of FIG. 52 with a partial cut away section.
Figure 55:
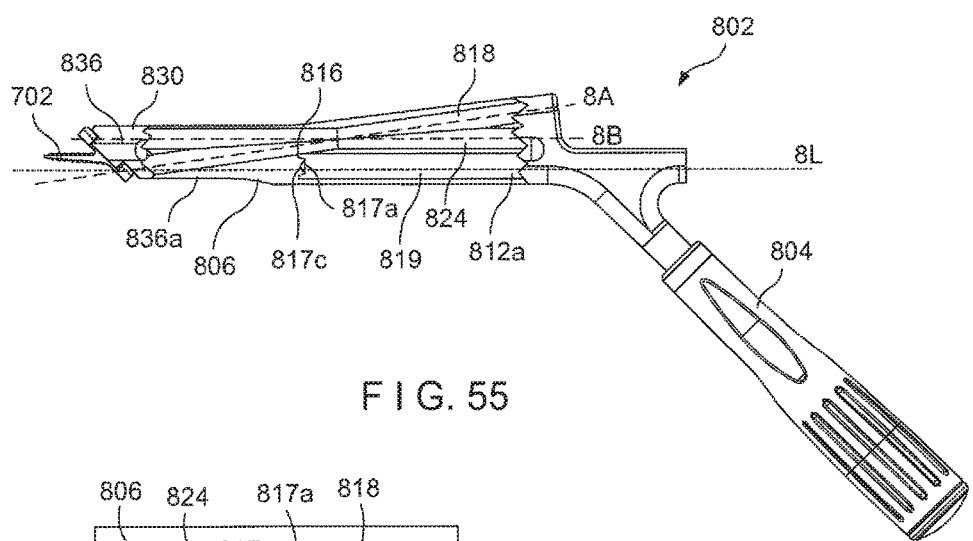
FIG. 55 shows a first partial cross-sectional view of the insertion instrument of FIG. 52.

The locking channel 812 extends parallel to the second screw channel 824 and parallel to the longitudinal axis 8L. As shown in FIG. 54, the proximal end 814 includes a threaded opening 814a extending into the locking channel 812. The locking channel 812 extends along a longitudinal axis 8L and is substantially cylindrical between the proximal end 814 and the increased width portion 832. From the increased width portion 832 to the distal end 816, the cylindrical shape of the locking channel 812 is divided into first and second channel portions 812a, 812b by the slot 830. The first and second channel portions 812a, 812b are half cylinders formed in the first and second compliant arms 836a, 836b, respectively.

As shown in FIGS. 54-56 and FIG. 59, the distal end 816 of the locking channel 812 has a locking bolt receiver 817 for receiving a locking bolt 840. The locking bolt receiver 817 has a cone-shape that tapers from a side wall 819 in a direction from its widest point at the distal end 816 to a proximally located narrowest point. That is, the locking bolt receiver 817 extends from the side wall 819 defining the locking channel 812 in a direction from the distal end 816 towards the proximal end 814 of the locking channel 812. The locking bolt receiver 817 is divided into first and second portions 817a, 817b by the slot 830. The first portion 817a of the locking bolt receiver 817 is formed in the first compliant arm 836a. The second portion 817b of the locking bolt receiver 817 is formed in the second compliant arm 836b. Planar surfaces 817c, 817d of the first and section portions 817a, 817b, respectively, face each other across the slot 830.

Figure 56:
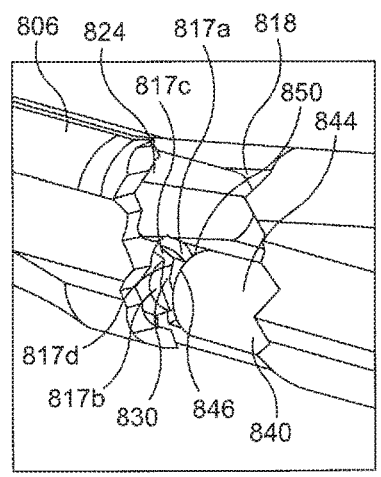
FIG. 56 shows a first zoomed partial cross-sectional view of the insertion instrument of FIG. 52 in a first operative configuration.
Figure 57:
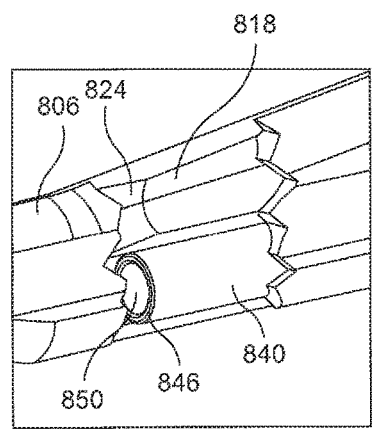
FIG. 57 shows a second zoomed partial cross-sectional view of the insertion instrument of FIG. 52 in the first a second operative configuration.
Figure 58:
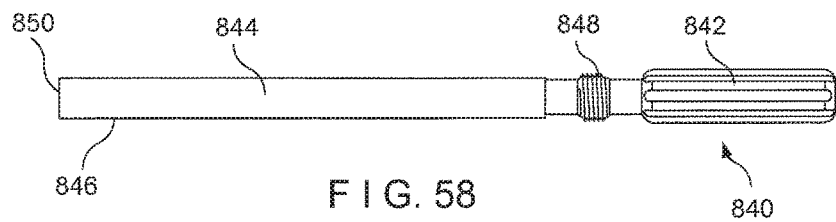
FIG. 58 shows a plan view of a locking bolt for use with the insertion instrument of FIG. 52.

FIGS. 56-60 show the locking bolt 840. The locking bolt 840 has a handle 842 in a proximal region from which a shaft 844 extends to a distal end 846 of the locking bolt 840. The handle 842 is knurled, grooved, etc., for ease of gripping by a user. In a region immediately distal to the handle 842, the shaft narrows and then widens again to a constant diameter section for the remainder of its length. In the narrow section, a threading 848 is formed. The threading 848 is configured to threadedly engage the thread formed in the threaded opening 814a for releasably coupling the locking bolt 840 to the locking channel 812. FIG. 57 shows a cone-shaped recess 850 formed in the distal end 846. The cone-shaped recess 850 is defined by an internal surface shaped to complement the outer surface of the cone-shaped locking bolt receiver 817.

Figure 59:
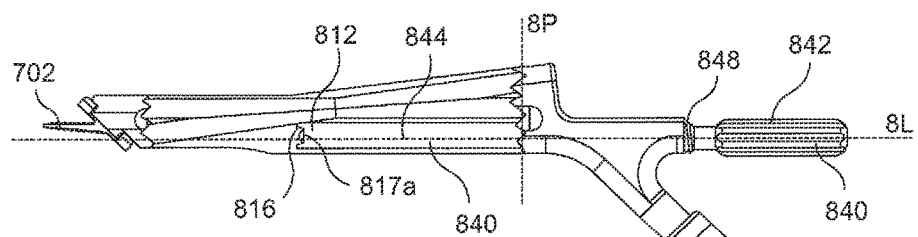
FIG. 59 shows a partial cross-sectional of the insertion instrument of FIG. 52 with the locking bolt of FIG. 58 in a first operative position.
Figure 60:
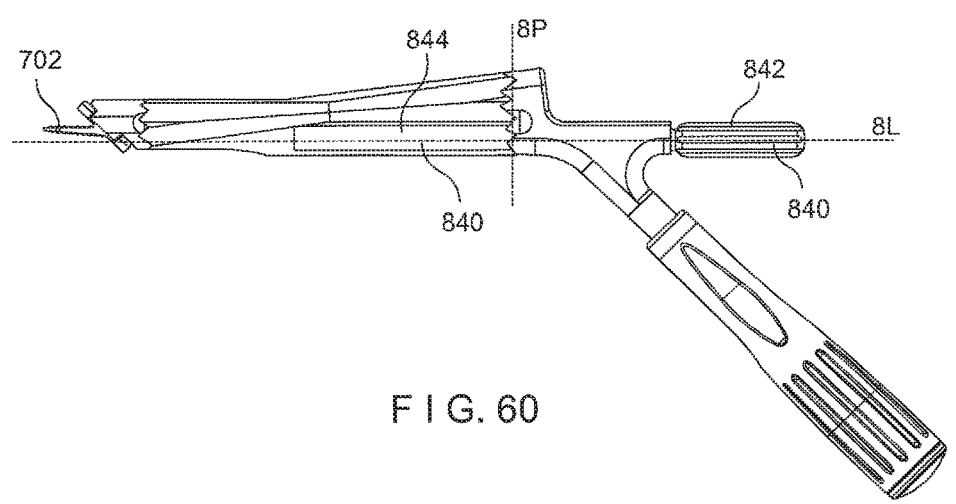
FIG. 60 shows a partial cross-sectional view of the locking bolt of FIG. 58 in a second operative position with the insertion instrument of FIG. 52.

The process by which the implant 702 is locked in the instrument 802 for insertion into a target position will now be described with reference to FIGS. 52 to 60. FIG. 52 shows an implant 702 being aligned with the instrument 802. In FIG. 52 the instrument 802 is in an open configuration. To fix the implant 702 in the instrument 802, the jaw 837 is first engaged with the recesses 796. Due to compliant nature of the arms 836a, 836b and the distance between the jaw members 837a, 837b, the jaw members 837a, 837b partially engage with the slots 796a, 796b to temporarily hold the implant 702 in the instrument. FIGS. 56 to 60 show how the locking bolt 840 is engaged with the locking bolt receiver 817 to transition the instrument 802 from the open configuration to the locked or gripping configuration in which the implant 702 is firmly held by the instrument 802 by the jaw 837. The locking bolt 840 is positioned through the locking channel 812 by inserting the shaft 844 into the threaded opening 814a and pushing the handle 842 until the threading 848 abuts the threaded opening 814a. The handle 842 is then rotated to engage the threading 848 with the thread of the threaded opening 814a. After a couple of rotations of the handle 842, the distal end 846 of shaft 844 has advanced towards the distal end 816 and locking bolt receiver 817 of the locking channel 812. FIGS. 56, 57 and 59 show the distal end 846 shortly before it engages with the locking bolt receiver 817. As shown by FIG. 60, the handle 842 continues to be rotated by a user until a point is reached where it can no longer be rotated, indicating that the implant 702 is firmly held. At this point, the inner cone 850 has engaged and slid over the outer cone of the locking bolt receiver 817 causing the distance between the planar surfaces 817c, 817d of the portions 817a, 817b to decrease. Since the portions 817a and 817b are part of the compliant arms 836a and 836b, this has the effect of narrowing the slot 830 and thereby reducing the distance between the jaw members 837a, 837b. As a consequence the jaw members 837a, 837b have been moved to a holding configuration where they have become firmly engaged in their respective slots 796a, 796b to firmly grip the implant 702 for guiding the implant 702 into a target position. As described in greater detail with respect to earlier embodiments, the implant 702 is secured to the insertion instrument 802 prior to insertion thereof into the body.

Figure 61:
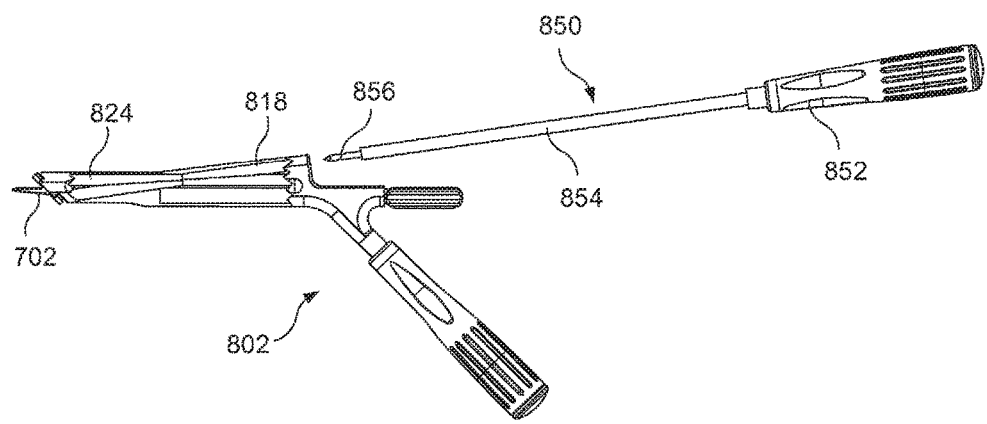
FIG. 61 shows an awl for use with the insertion instrument of FIG. 52 in a first operative position.
Figure 62:
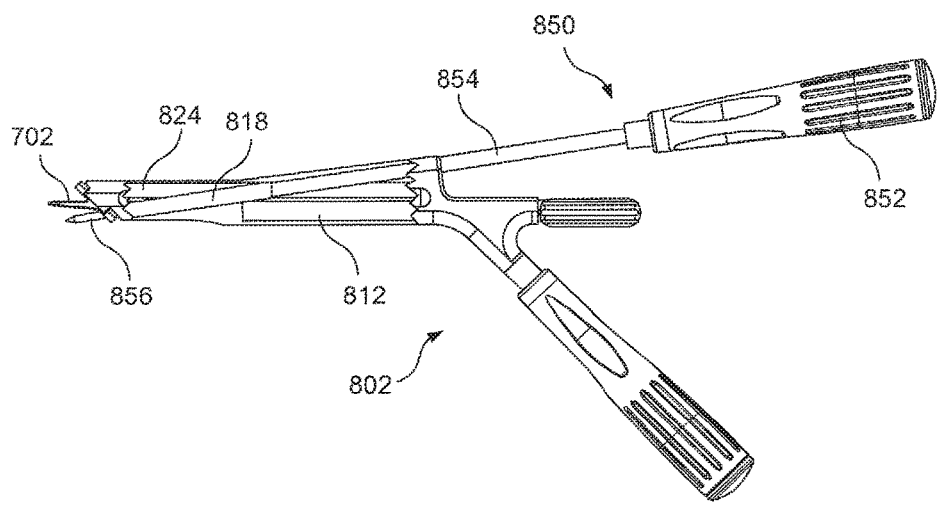
FIG. 62 shows the awl of FIG. 61 in a second operative position.

The insertion instrument 802 and implant 702 are guided to a target position adjacent target cervical vertebrae. As shown in FIGS. 61-62, an awl 850 known in the art is then inserted through each of the first and second channels 818, 824 and through each of the first and second openings 710, 712 to break the bone cortex and prepare the bone hole for the bone screws 708, 709. Specifically, as those skilled in the art will understand, the awl 850 extends from a proximal end comprising a handle 852 and along a shaft 854 to a sharpened portion 856 at a distal end, wherein a diameter of the shaft 854 substantially conforms to a diameter of the first and second channels 818, 824 and a diameter of the sharpened portion 856 substantially conforms to dimensions of the first and second bone screws 708, 709.

Figure 63:
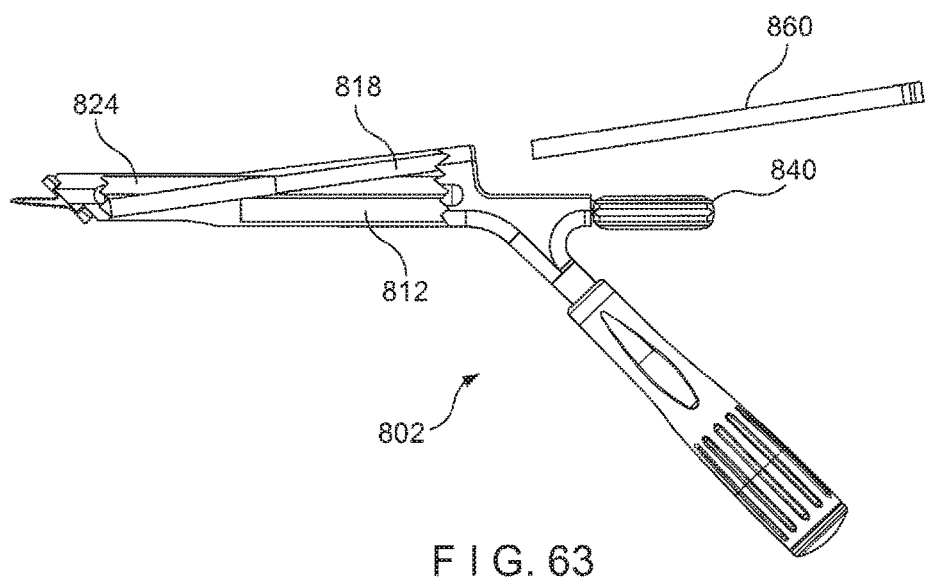
FIG. 63 shows a guide sleeve for use with the insertion instrument of FIG. 52 in a first operative position.
Figure 64:
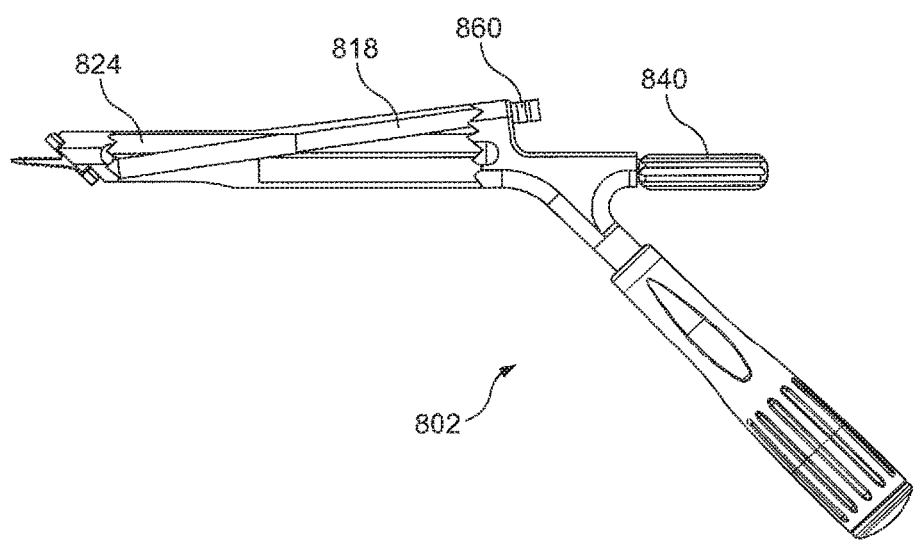
FIG. 64 shows the guide sleeve of FIG. 63 in a second operative position.
Figure 66:
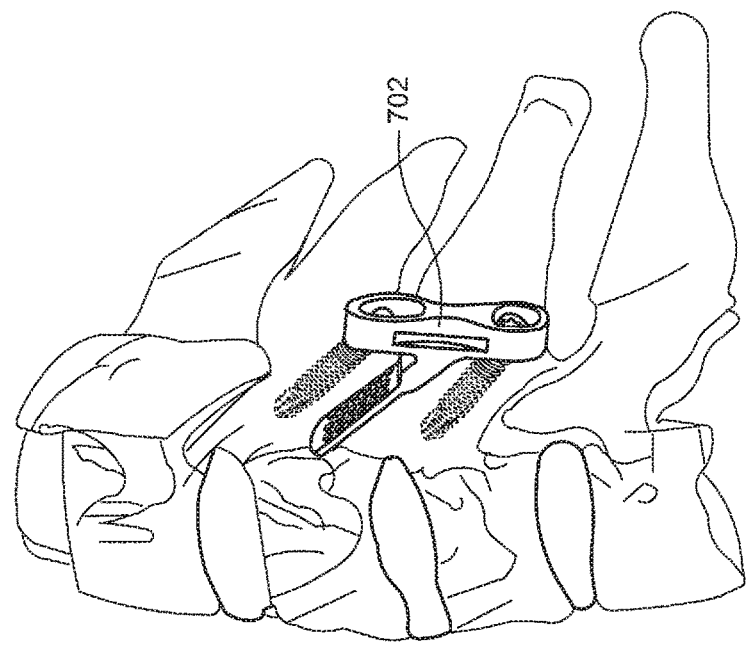
FIG. 66 shows a side view of the 3D computer model of FIG. 65.
Figure 65:
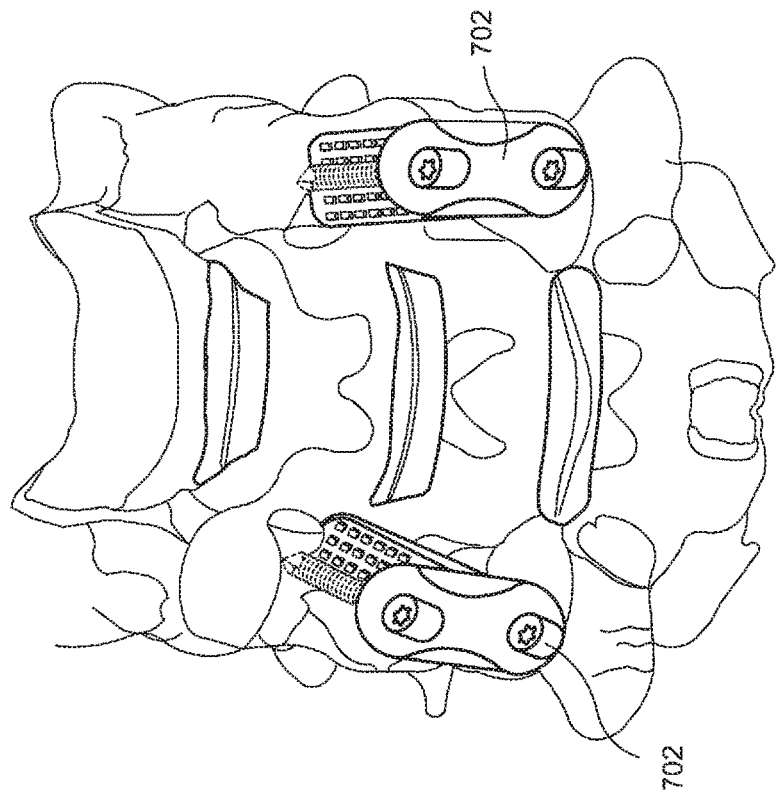
FIG. 65 shows a perspective view of a 3D computer model illustrating a portion of a cervical spine with first and second implants of FIG. 45 in situ.

As shown in FIGS. 63-64, a guide sleeve 860 is inserted into the first channel 818 to bridge an area where the first and second channels 818, 824 intersect. The guide sleeve 860 eliminates the risk of a bone screw inserted through the first channel 818 irretrievably falling off a screwdriver into the second channel 824 and vice versa. In accordance with an exemplary method according to the invention, the guide sleeve 860 is inserted into the first channel 818 to guide the insertion of the second bone screw 709 through the second opening 712 of the implant 702. Once the second bone screw 709 has been inserted, the guide sleeve 860 is removed and inserted into the second channel 824 to guide insertion of the first bone screw 708 into the first opening 710 of the implant 702. The first and second bone screws 708, 709 are then inserted into the implant 702 using a driving mechanism (not shown) known in the art. Once the first and second bone screws 708, 709 have been inserted to their respective target positions, the locking bolt 840 is unscrewed from the locking channel 812 and withdrawn proximally. The locking channel 812 returns to its original configuration due to the compliant nature of the arms 836a, 836b and thereby the slot 830 expands and the jaw transitions to the open configuration in which the implant 702 is loosely held. The implant 702 is then released and the insertion instrument 802 removed from the body leaving the implant 702 in position in the cervical spine as shown by FIGS. 65 and 66.

Figures 67, 68:
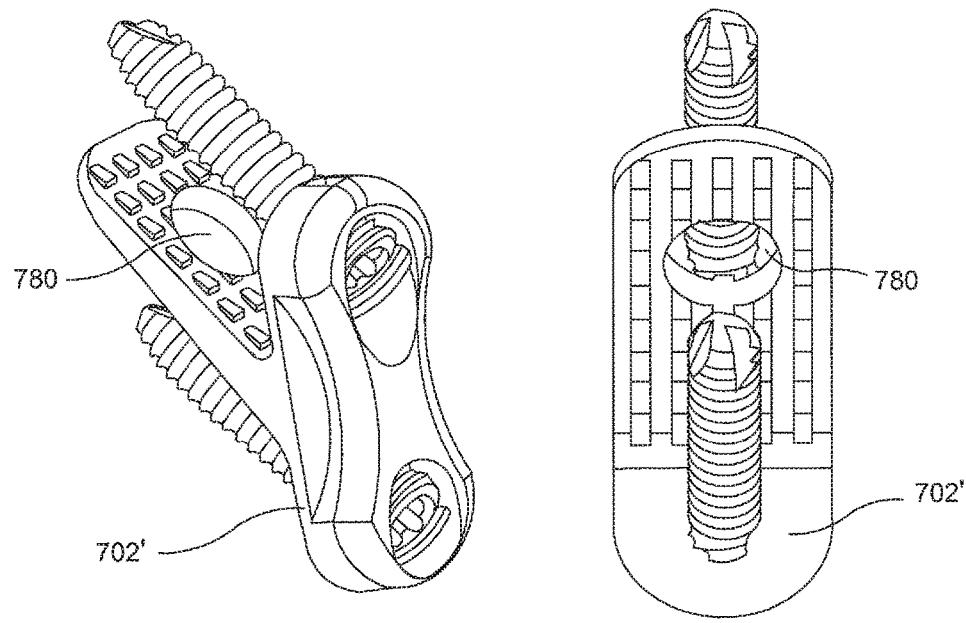
FIG. 67 shows a perspective view of an implant according to a still further exemplary embodiment of the invention.
FIG. 68 shows a front view of the implant of FIG. 67.
Figure 69:
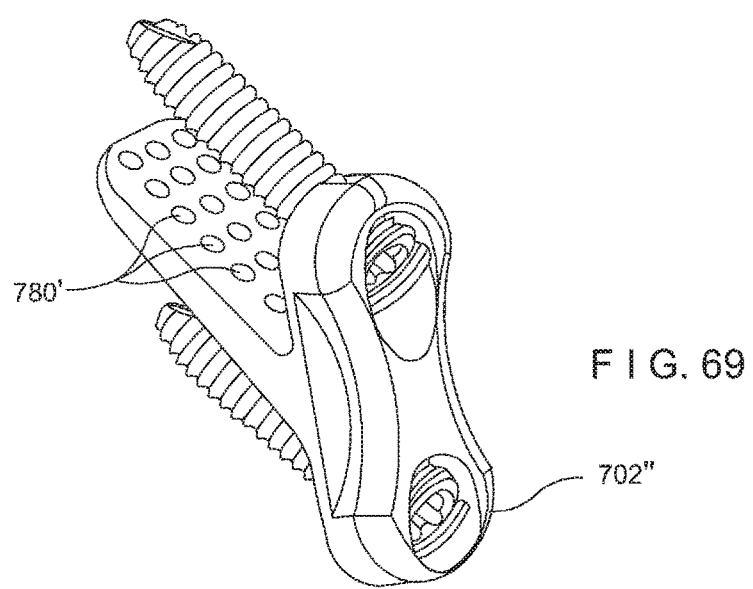
FIG. 69 shows a perspective view of an implant according to a yet still further exemplary embodiment of the invention.

FIGS. 67 and 68 show a further embodiment of the invention including an implant 702'. The implant 702' is substantially the same as the implant 702 with the exception of a hole 780 formed therein. FIG. 69 shows a still further embodiment of the invention including an implant 702", the implant features a plurality of holes 780' formed therein. FIG. 69 shows the implant 702" without the friction enhancing elements 792 of the implant 702, which can of course be provided as one of skill in the art would understand. As described in greater detail with respect to earlier embodiments, the hole 780 and plurality of holes 780' have the same purpose and function as the holes 480, 481.

Figure 70:
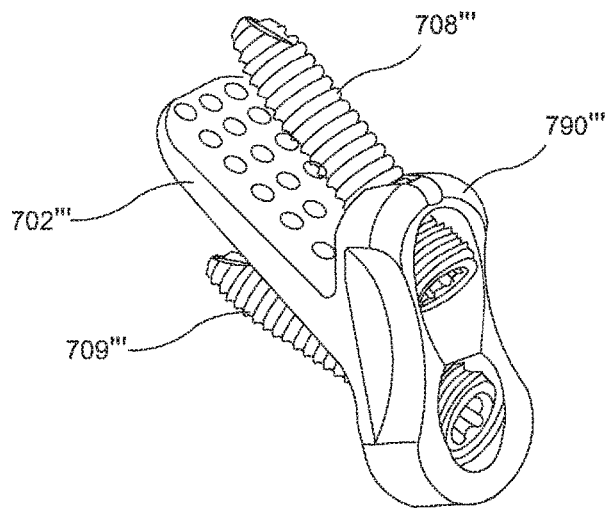
FIG. 70 shows a perspective view of an implant according to yet still another exemplary embodiment of the invention.
Figure 71:
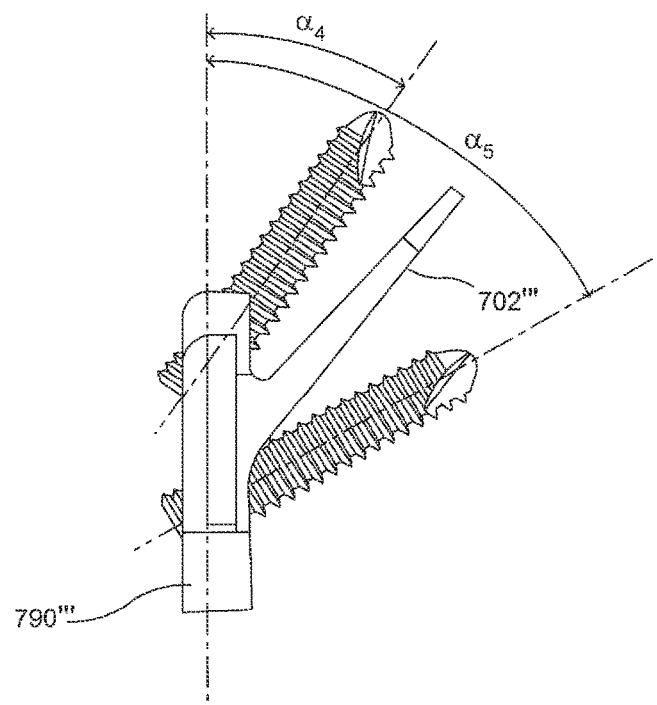
FIG. 71 shows a side view of the implant of FIG. 70.

FIGS. 70 and 71 show yet another embodiment of the invention including an implant 702'''. The implant 702''' is substantially the same as the implants 702, 702', 702" with the exception that a head portion 790''' thereof is smaller in comparison to the head section 790 described for the implant 702. As a consequence of the smaller head portion 790''', screw holes of the implant 702''' are angled such that screws 708''', 709''' inserted therethrough enter into the respective parts of the facet joints. With respect to the head portion 790''', the first screw 708''' is angled at $\alpha_4$ and the second screw 709''' is angled at $\alpha_5$ relative to the head portion 790'''. The angle $\alpha_4$ has a range of 20° to 90° and the angle $\alpha_5$ has a range of 40° to 120°.

It will be apparent to those skilled in the art that various modifications and variations can be made in the structure and the methodology of the present invention, without departing from the spirit or the scope of the invention. Thus, it is intended that the present invention cover the modifications and the variations of this invention provided that they come within the scope of the appended claims and their equivalents.

What is claimed:

1. A facet joint implant sized and shaped for insertion into a facet joint of the human spine, the facet joint implant comprising:
   a proximal end surface, and a distal end surface opposite the proximal end surface along a longitudinal direction;
   a first lateral surface, and a second lateral surface opposite the first lateral surface along a second direction perpendicular to the longitudinal direction, wherein the proximal and distal end surfaces and the first and second lateral surfaces define outermost peripheral surfaces of the implant;
   a first bone-engagement surface, and a second bone-engagement surface opposite the first bone-engagement surface along a third direction that is perpendicular to each of the longitudinal direction and the second direction, wherein the facet joint implant has a first height between the second bone-engagement surface and the first bone-engagement surface proximate the proximal end surface that is greater than a second height between the second and the first bone-engagement surfaces proximal the distal end surface, the facet joint implant having a cut out extending from the distal end surface toward the proximal end surface and from the first bone-engagement surface to the second bone-engagement surface such that the cut out extends through the first and second bone-engagement surfaces, the cut out defined by first and second inner lateral walls spaced from one another along the second direction such that the first inner lateral wall is disposed between the first lateral surface and the second inner lateral wall, the cut out further defined by a back wall connected between the first and second inner lateral walls such that the facet joint implant defines 1) a first distal portion section that is located between the first lateral surface and the first inner lateral wall, and 2) a second distal portion section that is located between the second lateral surface and the second inner lateral wall, wherein each of the first and second distal portion sections define a respective opening that extends from the first bone-engagement surface to the second bone-engagement surface to promote bony growth;
   a central opening extending through the facet joint implant along the longitudinal direction from the proximal end surface through the back wall of the cut out, the central opening sized and configured to accept a guidewire for insertion into a facet joint, wherein the central opening extends along a longitudinal axis;
   a first bone fixation element hole extending from the proximal end surface and through the facet joint implant, the first bone fixation element hole overlapping with the central opening, wherein the first bone fixation element hole defines a first angle with respect to the longitudinal axis, the first angle being between 10° and 45°; and a second bone fixation element hole extending from the proximal end surface and through the facet joint implant, the second bone fixation element hole overlapping with the central opening, wherein the second bone fixation element hole defines a second angle with respect to the longitudinal axis, the second angle being between 10° and 45°.

2. The facet joint implant of claim 1, further comprising at least one rib that extends out from the first bone-engagement surface of the first distal portion section and that is elongate in a direction that extends from the proximal end surface to the distal end surface.

3. The facet joint implant of claim 1, further comprising at least one rib extending out from the second bone-engagement surface of the first distal portion section and that is elongate in a direction that extends from the proximal end surface to the distal end surface.

4. The facet joint implant of claim 1, further comprising at least one rib that extends out from the first bone-engagement surface of the second distal portion section and that is elongate in a direction that extends from the proximal end surface to the distal end surface.

5. The facet joint implant of claim 1, further comprising at least one rib that extends out from the second bone-engagement surface of the second distal portion section and that is elongate in a direction that extends from the proximal end surface to the distal end surface.

6. The facet joint implant of claim 1, further comprising at least one rib that extends out from each of the first and second bone-engagement surfaces of each of the first and second distal portion sections, wherein each rib is elongate in a direction that extends from the proximal end surface to the distal end surface.

7. The facet joint implant of claim 1 wherein the facet joint implant is in the form of a tapered wedge-shape from the proximal end surface to the distal end surface.

8. The facet joint implant of claim 7 wherein the distal end surface has a blunt profile.

9. The facet joint implant of claim 1 wherein the first and second lateral surfaces each have a recess located adjacent the proximal end surface and each recess has a means for engaging an insertion tool defining an axis of rotation about which the facet joint implant can pivot relative to the insertion tool.

10. The facet joint implant of claim 1 wherein the first bone fixation element hole is threaded.

11. The facet joint implant of claim 1 wherein the first and second bone fixation element holes are threaded.

12. The facet joint implant of claim 1 wherein each of the first and second lateral surfaces of the facet joint implant when traced from the second end toward the first end curves in a convex-shaped arc and then in a concave-shaped arc.

13. The facet joint implant of claim 12 wherein the transition from the convex-shaped arc to the concave-shaped arc for the first lateral surface is located past the opening in the first distal portion.

14. The facet joint implant of claim 13 wherein the transition from the convex-shaped arc to the concave-shaped arc for the second lateral surface is located past the opening in the second distal portion.

15. The facet joint implant of claim 14 wherein the first and second bone-engagement surfaces of each of the first and second distal portions have a plurality of ribs that extend outward therefrom and are elongate along a direction that extends from the proximal end to the distal end.

16. The facet joint implant of claim 15 wherein each of the ribs has a plurality of teeth extending therefrom.

17. The facet joint implant according to claim 1, wherein the first and second distal portion sections terminate at first and second free ends, respectively, defined at the distal end surface.

18. An implant sized and shaped for insertion into a facet joint of the human spine, the implant comprising:
  a proximal end surface and a distal end surface, the proximal and distal end surfaces spaced from one another along a longitudinal direction;
  a first outer lateral surface and a second outer lateral surface, the first and second outer lateral surfaces spaced from one another along a second direction, perpendicular to the longitudinal direction, wherein the proximal and distal end surfaces and the first and second outer lateral surfaces define outermost peripheral surfaces of the implant;
  a first bone-engagement surface and a second bone-engagement surface, the first and second bone-engagement surfaces spaced from one another along a third direction, perpendicular to both the longitudinal and second directions;
  a first inner lateral surface, and a second inner lateral surface that faces the first inner lateral surface so as to define a cut out therebetween that extends from the distal end surface toward the proximal end surface and from the first bone-engagement surface to the second bone-engagement surface such that the cut out forms a discontinuity in each of the distal end surface and the first and second bone-engagement surfaces;
  a plurality of ribs, each extending out from a respective one of the first and second bone-engagement surfaces along the third direction, such that each rib is elongate from its proximal end to its distal end;
  wherein the implant defines a first bone fixation element receiving opening extending through the proximal end surface along a first axis oriented and configured to align with a first one of the vertebra of the facet joint when the implant is inserted into the facet joint; and
  further comprising a guidewire receiving channel extending through the implant along the longitudinal direction from the proximal end surface through a back wall of the cut out connected between the first and second inner lateral surfaces defining the cut out, a portion of the guidewire receiving channel intersecting the first bone fixation element receiving opening such that the guidewire receiving channel is sized and configured to accept a guidewire that blocks a bone fixation element from passing through the first bone fixation element receiving opening.

19. The implant according to claim 18, further comprising a second bone fixation element receiving opening extending through the proximal end surface along a second axis oriented and configured to align with a second one of the vertebra of the facet joint when the implant is inserted into the facet joint.

20. The implant according to claim 19, wherein the first and second bone fixation holes are spaced from one another along the third direction.

21. The implant according to claim 19, wherein the first and second axes are angled relative to one another.

22. The implant according to claim 21, wherein the first and second axes extend at acute angles with respect to a longitudinal axis of the implant.

23. The implant according to claim 19, wherein the first bone fixation element receiving opening extends through the first bone-engagement surface of the implant and the second bone fixation element receiving opening extends through the second bone-engagement surface of the implant.

24. The implant according to claim 18, wherein the first and second bone-engagement surfaces are sized and shaped to form an interference fit when received within a facet joint in a desired configuration.

25. The implant according to claim 18, wherein the first and second bone-engagement surfaces taper between the proximal end surface and the distal end surface such that the implant has a wedge shape.

26. The implant according to claim 18, wherein the distal end surface has a blunt profile.

27. The implant according to claim 18, wherein proximal portions of the first and second bone-engagement surfaces are parallel to one another and the first and second bone-engagement surfaces taper from the proximal portions toward the distal end surface.

28. The implant according to claim 18, further comprising a plurality of protrusions on the implant extending along the plurality of ribs.

29. The implant according to claim 28, wherein the protrusions include one of a jagged and saw-toothed edge.

30. The implant according to claim 18, wherein a proximal end of the implant includes at least one abutting surface which, when the implant is coupled to an insertion tool, abuts a surface thereof to indicate an alignment of the first bone fixation element receiving opening with a first guide opening of the insertion tool.

31. The implant according to claim 18, wherein a proximal end of the implant includes a first protrusion and a second protrusion configured to engage an insertion tool, the first and second protrusions defining an axis of rotation about which the implant may pivot relative to the insertion tool.

32. The implant according to claim 18, further comprising a plurality of holes extending through the first and second bone-engagement surfaces.

33. The implant according to claim 18, wherein the back wall is connected between the first and second inner lateral surfaces such that a first distal portion section of the implant is located between the first outer lateral surface and the first inner lateral surface and a second distal portion section is located between the second outer lateral surface and the second inner lateral surface, wherein the first distal portion is spaced from the second distal portion by the cut out.

34. The implant according to claim 33, wherein each of the first and second distal portion sections include an opening extending from the first bone-engagement surface to the second bone-engagement surface.

35. The implant according to claim 18, further comprising a stop arranged on the implant to control an insertion depth of the implant in a facet joint.

36. The implant according to claim 18, comprising a body portion that includes the first and second bone-engagement surfaces, the first and second outer lateral surfaces, and the distal end surface, the implant further comprising a head portion attached to a first end of the body portion such that the first bone fixation element receiving opening extends through the head portion.

37. An implant sized and shaped for insertion into a facet joint of the human spine, the implant comprising:
   a proximal end surface and a distal end surface, the proximal and distal end surfaces spaced from one another along a longitudinal direction;
   a first outer lateral surface and a second outer lateral surface, the first and second outer lateral surfaces spaced from one another along a second direction, perpendicular to the longitudinal direction, wherein the proximal and distal end surfaces and the first and second outer lateral surfaces define outermost peripheral surfaces of the implant;
   a first bone-engagement surface and a second bone-engagement surface, the first and second bone-engagement surfaces spaced from one another along a third direction, perpendicular to both the longitudinal direction and the second direction; and
   a first inner lateral surface, and a second inner lateral surface that faces the first inner lateral surface so as to define a cut out therebetween that extends from the distal end surface toward the proximal end surface and from the first bone-engagement surface to the second bone-engagement surface such that the cut out forms a discontinuity in each of the distal end surface and the first and second bone-engagement surfaces, wherein the implant defines a first bone fixation element receiving opening extending through the proximal end surface along a first axis oriented and configured to align with a first one of the vertebra of the facet joint when the implant is inserted into the facet joint;
   and wherein the implant defines a central opening that extends through the implant along the longitudinal direction from the proximal end surface through a back wall connecting the first and second inner lateral surfaces that define the cut out, a portion of the central opening intersecting the first bone fixation element receiving opening, the central opening being sized and configured to accept a guidewire that blocks a bone fixation element from passing through the first bone fixation element receiving opening.

38. The implant according to claim 37, further comprising a second bone fixation element receiving opening extending through the proximal end surface along a second axis oriented and configured to align with a second one of the vertebra of the facet joint when the implant is inserted into the facet joint, wherein the central opening intersects the second bone fixation element receiving opening, the central opening being sized and configured to accept a guidewire that blocks a bone fixation element from passing through the second bone fixation element receiving opening.

39. The implant according to claim 38, wherein the first and second axes are angled relative to one another.

40. The implant according to claim 38, wherein the first bone fixation element receiving opening extends through the first bone-engagement surface of the implant and the second bone fixation element receiving opening extends through the second bone-engagement surface of the implant.

41. The implant according to claim 38, wherein the first and second axes extend at acute angles with respect to a longitudinal axis of the implant.

42. The implant according to claim 37, wherein the first and second bone-engagement surfaces are sized and shaped to form an interference fit when received within a facet joint in a desired configuration.

43. The implant according to claim 37, wherein the first and second bone-engagement surfaces taper between the proximal end surface and the distal end surface such that the implant has a wedge shape.

44. The implant according to claim 37, wherein proximal portions of the first and second bone-engagement surfaces are parallel to one another and the first and second bone-engagement surfaces taper from the proximal portions toward the distal end surface.

45. The implant according to claim 37, wherein the distal end surface has a blunt profile.

46. The implant according to claim 37, further comprising a plurality of ribs that extend from at least one of the first and second bone-engagement surfaces, each rib extending along a direction from the proximal end surface to the distal end surface.

47. The implant according to claim 46, further comprising a plurality of protrusions on the implant extending along the plurality of ribs.

48. The implant according to claim 37, wherein a proximal end of the implant includes at least one abutting surface which, when the implant is coupled to an insertion tool, abuts a surface thereof to indicate an alignment of the first bone fixation element receiving opening with a first guide opening of the insertion tool.

49. The implant according to claim 37, further comprising a plurality of holes extending through the first and second bone-engagement surfaces.

50. The implant according to claim 37, wherein the back wall connects the first and second inner lateral surfaces such that a first distal portion section of the implant is located between the first lateral surface and the first inner lateral surface and a second distal portion section is located between the second lateral surface and the second inner lateral surface, wherein the first distal portion is spaced from the second distal portion by the cut out.

51. The implant according to claim 50, wherein each of the first and second distal portion sections include an opening extending from the first bone-engagement surface to the second bone-engagement surface.

52. The implant according to claim 37, further comprising a stop arranged on the implant to control an insertion depth of the implant in a facet joint.

53. The implant according to claim 37, comprising a body portion that includes the first and second bone-engagement surfaces, the first and second outer lateral surfaces, and the distal end surface, the implant further comprising a head portion attached to a first end of the body portion such that the first bone fixation element receiving opening extends through the head portion.

54. The implant according to claim 37, wherein the central opening extends along a central axis that extends from the proximal end surface to the distal end surface and between the first bone-engagement surface and the second bone-engagement surface.

55. The implant according to claim 37, wherein the first and second bone fixation holes are spaced from one another along the third direction.

* * * * *